United States Patent
Zeldis

(10) Patent No.: US 7,354,948 B2
(45) Date of Patent: Apr. 8, 2008

(54) METHODS FOR TREATMENT OF CHRONIC UVEITIS USING CYCLOPROPYL-N-{2-[(1S)-1-(3-ETHOXY-4-METHOXYPHENYL)-2-(METHYLSULFONYL)ETHYL]-3-OXOISOINDOLINE-4-YL} CARBOXAMIDE

(75) Inventor: Jerome B. Zeldis, Princeton, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 10/534,325

(22) PCT Filed: Nov. 6, 2003

(86) PCT No.: PCT/US03/35545

§ 371 (c)(1),
(2), (4) Date: Sep. 12, 2005

(87) PCT Pub. No.: WO2004/043378

PCT Pub. Date: May 27, 2004

(65) Prior Publication Data

US 2006/0035955 A1    Feb. 16, 2006

Related U.S. Application Data

(60) Provisional application No. 60/424,601, filed on Nov. 6, 2002.

(51) Int. Cl.
*A61K 31/40* (2006.01)
*A01N 43/38* (2006.01)

(52) U.S. Cl. .................. 514/411; 514/412; 514/416; 514/417

(58) Field of Classification Search ............ 514/412, 514/416, 417
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni et al. | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,810,643 A | 3/1989 | Souza | |
| 4,999,291 A | 3/1991 | Souza | |
| 5,059,595 A | 10/1991 | Le Grazie | |
| 5,073,543 A | 12/1991 | Marshall et al. | |
| 5,120,548 A | 6/1992 | McClelland et al. | |
| 5,134,127 A | 7/1992 | Stella et al. | |
| 5,229,496 A | 7/1993 | Deeley et al. | |
| 5,354,556 A | 10/1994 | Sparks et al. | |
| 5,385,901 A | 1/1995 | Kaplan et al. | |
| 5,391,485 A | 2/1995 | Deeley et al. | |
| 5,393,870 A | 2/1995 | Deeley et al. | |
| 5,463,063 A | 10/1995 | Muller | |
| 5,528,823 A | 6/1996 | Rudy, Jr. et al. | |
| 5,580,755 A | 12/1996 | Souza | |
| 5,591,767 A | 1/1997 | Mohr et al. | |
| 5,605,914 A | 2/1997 | Muller | |
| 5,639,476 A | 6/1997 | Oshlack et al. | |
| 5,658,940 A | 8/1997 | Muller et al. | |
| 5,674,533 A | 10/1997 | Santus et al. | |
| 5,698,579 A | 12/1997 | Muller | |
| 5,703,098 A | 12/1997 | Muller et al. | |
| 5,712,291 A | 1/1998 | A'Amato | |
| 5,728,844 A | 3/1998 | Muller et al. | |
| 5,728,845 A | 3/1998 | Muller et al. | |
| 5,731,325 A | 3/1998 | Andrulis, Jr. et al. | |
| 5,733,566 A | 3/1998 | Lewis | |
| 5,736,570 A | 4/1998 | Muller et al. | |
| 5,801,195 A | 9/1998 | Muller et al. | |
| 5,877,200 A | 3/1999 | Muller | |
| 5,929,117 A | 7/1999 | Muller et al. | |
| 5,955,476 A | 9/1999 | Muller et al. | |
| 5,968,945 A | 10/1999 | Muller et al. | |
| 6,011,050 A | 1/2000 | Muller et al. | |
| 6,015,557 A | 1/2000 | Tobinick et al. | |
| 6,020,358 A | 2/2000 | Muller et al. | |
| 6,046,221 A | 4/2000 | Muller et al. | |

(Continued)

FOREIGN PATENT DOCUMENTS

WO    WO 95/01348    1/1995

(Continued)

OTHER PUBLICATIONS

Dredge et al., 2003, "Angiogenesis inhibitors in cancer therapy," Curr. Opin. Investig. Drugs 4(6):667-673.

(Continued)

*Primary Examiner*—Ardin H. Marschel
*Assistant Examiner*—Shirley V Gembeh
(74) *Attorney, Agent, or Firm*—Jones Day

(57) ABSTRACT

Methods of treating, preventing and/or managing cancer as well as and diseases and disorders associated with, or characterized by, undesired angiogenesis are disclosed. Specific methods encompass the administration of a selective cytokine inhibitory drug alone or in combination with a second active ingredient. The invention further relates to methods of reducing or avoiding adverse side effects associated with chemotherapy, radiation therapy, hormonal therapy, biological therapy or immunotherapy which comprise the administration of a selective cytokine inhibitory drug. Pharmaceutical compositions, single unit dosage forms, and kits suitable for use in methods of the invention are also disclosed.

13 Claims, No Drawings

U.S. PATENT DOCUMENTS

| | | |
|---|---|---|
| 6,075,041 A | 6/2000 | Muller |
| 6,114,355 A | 9/2000 | D'Amato |
| 6,130,226 A | 10/2000 | Muller et al. |
| 6,140,346 A | 10/2000 | Andrulis, Jr. et al. |
| 6,177,077 B1 | 1/2001 | Tobinick |
| 6,180,644 B1 | 1/2001 | Muller et al. |
| 6,200,987 B1 | 3/2001 | Muller |
| 6,214,857 B1 | 4/2001 | Muller et al. |
| 6,235,756 B1 | 5/2001 | D'Amato |
| 6,262,101 B1 | 7/2001 | Muller et al. |
| 6,284,780 B1 | 9/2001 | Muller et al. |
| 6,326,388 B1 | 12/2001 | Man et al. |
| 6,379,666 B1 | 4/2002 | Tobinick |
| 6,380,239 B1 | 4/2002 | Muller et al. |
| 6,395,754 B1 | 5/2002 | Muller et al. |
| 6,403,613 B1 | 6/2002 | Man et al. |
| 6,419,934 B1 | 7/2002 | Tobinick |
| 6,419,944 B2 | 7/2002 | Tobinick |
| 6,420,414 B1 | 7/2002 | D'Amato |
| 6,423,321 B2 | 7/2002 | Tobinick |
| 6,428,787 B1 | 8/2002 | Tobinick |
| 6,429,221 B1 | 8/2002 | Muller et al. |
| 6,458,810 B1 | 10/2002 | Muller et al. |
| 6,469,045 B1 | 10/2002 | D'Amato |
| 6,471,961 B1 | 10/2002 | Tobinick |
| 6,479,554 B2 | 11/2002 | Muller et al. |
| 6,518,281 B2 | 2/2003 | Muller et al. |
| 6,518,298 B2 | 2/2003 | Green et al. |
| 6,537,549 B2 | 3/2003 | Tobinick |
| 6,623,736 B2 | 9/2003 | Tobinick |
| 6,667,316 B1 | 12/2003 | Man et al. |
| 6,699,899 B1 | 3/2004 | Man et al. |
| 2001/0004456 A1 | 6/2001 | Tobinick |
| 2001/0016195 A1 | 8/2001 | Tobinick |
| 2001/0018445 A1 | 8/2001 | Huang et al. |
| 2001/0026801 A1 | 10/2001 | Tobinick |
| 2001/0056114 A1 | 12/2001 | D'Amato |
| 2002/0035090 A1 | 3/2002 | Zeldis et al. |
| 2002/0045643 A1 | 4/2002 | Muller et al. |
| 2002/0052398 A1 | 5/2002 | D'Amato |
| 2002/0054899 A1 | 5/2002 | Zeldis |
| 2002/0061923 A1 | 5/2002 | D'Amato |
| 2002/0128228 A1 | 9/2002 | Hwu |
| 2002/0131954 A1 | 9/2002 | Tobinick |
| 2002/0131955 A1 | 9/2002 | Tobinick |
| 2002/0161023 A1 | 10/2002 | D'Amato |
| 2002/0173658 A1 | 11/2002 | Muller et al. |
| 2002/0183360 A1 | 12/2002 | Muller et al. |
| 2003/0007972 A1 | 1/2003 | Tobinick |
| 2003/0013739 A1 | 1/2003 | Masferrer et al. |
| 2003/0028028 A1 | 2/2003 | Man et al. |
| 2003/0049256 A1 | 3/2003 | Tobinick |
| 2003/0069428 A1 | 4/2003 | Muller et al. |
| 2003/0113318 A1 | 6/2003 | Tobinick |
| 2003/0139451 A1 | 7/2003 | Shah et al. |
| 2003/0144325 A1 | 7/2003 | Muller et al. |
| 2003/0181428 A1 | 9/2003 | Green et al. |
| 2003/0185826 A1 | 10/2003 | Tobinick |
| 2003/0187024 A1 | 10/2003 | D'Amato |
| 2003/0187052 A1 | 10/2003 | Schafer et al. |
| 2003/0191098 A1 | 10/2003 | D'Amato |
| 2003/0235909 A1 | 12/2003 | Hariri et al. |
| 2004/0029832 A1 | 2/2004 | Zeldis |
| 2004/0077685 A1 | 4/2004 | Figg et al. |
| 2004/0077686 A1 | 4/2004 | Dannenberg et al. |
| 2004/0087546 A1 | 5/2004 | Zeldis |
| 2004/0091455 A1 | 5/2004 | Zeldis |
| 2004/0122052 A1 | 6/2004 | Muller et al. |
| 2004/0127545 A1 | 7/2004 | Green et al. |
| 2004/0167199 A1 | 8/2004 | Muller et al. |
| 2004/0254214 A1 | 12/2004 | Man et al. |
| 2004/0259873 A1 | 12/2004 | Man et al. |
| 2004/0266809 A1 | 12/2004 | Emanuel et al. |
| 2005/0014727 A1 | 1/2005 | Muller et al. |

FOREIGN PATENT DOCUMENTS

| | | |
|---|---|---|
| WO | WO 97/08143 | 3/1997 |
| WO | WO 97/23457 | 7/1997 |
| WO | WO 99/06041 | 2/1999 |
| WO | WO 01/34606 | 5/2001 |
| WO | WO 01/45702 | 6/2001 |
| WO | WO 01/70275 | 9/2001 |
| WO | WO 01/87307 | 11/2001 |
| WO | WO 02/064083 | 8/2002 |
| WO | WO 03/080048 | 10/2003 |
| WO | WO 03/080049 | 10/2003 |
| WO | WO 03/086373 | 10/2003 |

OTHER PUBLICATIONS

Dredge et al., 2002, "Immunological effects of thalidomide and its chemical and functional analogs," Crit. Rev. Immunol. 22(5-6):425-437.

Dredge et al., 2002, "Recent developments in antiangiogenic therapy," Expert Opin. Biol. Ther. 2(8):953-966.

Gee et al., 2003, "Selective cytokine inhibitory drugs with enhanced antiangiogenic activity control tumor growth through vascular inhibition," Cancer Res. 63(23):8073-8078.

Marriott et al., 2001, "Immunotherapeutic and antitumour potential of thalidomide analogues," Expert Opin. Biol. Ther. 1(4):1-8.

Marriott et al., 2002, "Thalidomide and its analogues have distinct and opposing effects on TNF-alpha and TNFR2 during co-stimulation of both CD4(+) and CD8(+) T cells," Clin. Exp. Immunol. 130(1):75-84.

Molostvov et al., 2004, "The effects of selective cytokine inhibitory drugs (CC-10004 and CC-1088) on VEGF and IL-6 expression and apoptosis in myeloma and endothelial cell co-cultures," Br. J. Haematol. 124(3):366-375.

Zeldis et al., 2003, " Potential new therapeutics for Waldenstrom's macroglobulinemia," Semin. Oncol. 30(2):275-281.

Database NLDB XP002371400 retrieved from STN. Database accession No. 2002:87776, & BIOWORLD Today, vol. 13, No. 68. Apr. 10, 2002.

Database Phin "Celgene moving beyond Thalidomid" XP002371401 retrieved from STN. Database accession No. 2001:12958, & SCRIP (Newsletter), No. 2657 p. 12. Jul. 4, 2001.

Li et al., "Tumor angiogenesis: Molecular pathology, therapeutic targeting, and imaging," 2000, Academic Radiology, 7(10):800-811.

Oliver et al., "Thalidomide analogue CC1069 inhibits development of rat adjuvant arthritis," 1999, Clinical and Experimental Immunology, 118(2):315-321.

U.S. Appl. No. 60/499,723, filed Sep. 4, 2003, Markian.
U.S. Appl. No. 60/454,149, filed Mar. 12, 2003, Man et al.
U.S. Appl. No. 60/452,460, filed Mar. 5, 2003, Muller et al.
U.S. Appl. No. 60/438,450, filed Jan. 7, 2003, Muller et al.
U.S. Appl. No. 60/438,448, filed Jan. 7, 2003, Muller et al.
U.S. Appl. No. 60/372,348, filed Apr. 12, 2002, Hariri et al.
U.S. Appl. No. 10/748,085, filed Dec. 29, 2003, Zhang et al.
U.S. Appl. No. 09/545,654, filed Apr. 10, 2000, D'Amato.
U.S. Appl. No. 09/287,377, filed Apr. 7, 1999, D'Amato.

Alexanian et al., 2004, "VTD (Velcade, thalidomide, dexamethasone) as primary therapy for newly-diagnosed multiple myeloma," Am. Soc. Hematol. 46th Ann. Meeting Dec. 4-7, 2004, San Diego, CA Abstract #210.

Anderson, 2000, "Thalidomide: Therapeutic potential in hematologic malignancies," Seminars in Hematology 37(1 Supp 3): 1-4.

Attal et al., 2004, "Maintenance treatment with thalidomide after autologous transplantation for myeloma: First analysis of a prospective randomized study of the Intergroupe Francophone du Myelome (IFM 99 02)," Am. Soc. Hematol. 46th Ann. Meeting Dec. 4-7, 2004, San Diego, CA Abstract #535.

Bach, 1963, "Thalidomide in Cancer Chemotherapy," *The Lancet*, Jun. 8, No. 1271, pg. 71.

Bach, 1963, "Studies on the Possible Anti-Neoplastic Effect of Thalidomide," *Acta Pathologica Et Microbiologica Scandinavica* 59:491-499.

Bernardeschi et al., 2003, "Low dose thalidomide plus monthly high-dose oral dexamethasone (thali-dexa): Results, prognostic factors and side effects in eight patients previously treated with multiple myeloma," J. Exp. Clin. Cancer Res. 22(Supp 4):129-133.

Cartensen, 1995, Drug Stability: Principles & Practice, 2nd ed., New York pp. 379-380.

Chaundhry, 1966, "Effect of Prednisolone and Thalidomide on Induced Submandibular Gland Tumors in Hamster," *Cancer Research* 26(part 1)1884-86.

Corral et al., 1999, "Immunomodulation by thalidomide and thalidomide analogues," Ann. Rheum. Dis. 58(Suppl 1):I107-113.

Craig et al., 1967, "Potential anticancer agents. III. 2-phthalimidoaldehydes and derivatives," Potential Anticancer Agents III 10:1071-1073.

D'Amato et al., 2001, "Mechanism of action of thalidomide and 3-aminothalidomide in multiple myeloma," Semin. Oncol. 28:597-601.

D'Amato et al., 1994, "Thalidomide is an Inhibitor of Angiogenesis", Proc. Natl. Acad. Sci. 91:4082-4085.

Davies et al., 2001, "Thalidomide and immunomodulatory derivatives augment natural killer cell cytotoxicity in multiple myeloma," Blood 98(1):210-216.

De et al., 1976, "Hansch analysis for some antineoplastic glutarimides," J. Indian Chem. Soc. I.III: 825-826.

De et al., 1976, "Possible antineoplastic agents: III. Synthesis of 6-alkyl-2-[4'-methoxyphthalimido] and 6-alkyl-3-[3'-4'-dimethoxyphenyl] glutarimides," J. Indian Chem. Soc. I.III:1122-1125.

Dimopoulos et al., 2004, "Primary treatment with puilsed melphalan, dexamethasone, thalidomide (MDT) for symptomatic patients with multiple myeloma ≧75 years of age," Am. Soc. Hematol. 46th Ann. Meeting Dec. 4-7, 2004, San Diego, CA Abstract #1482.

DiPaolo, Jun. 26, 1964, "Thalidomide: Effects on Ehrlich Ascites Tumor Cells in vitro" Science 144:1583.

DiPaolo, 1963, "Effect of Thalidomide on a Variety of Transplantable Tumors," *Cancer Chemotherapy Reports* No. 29, p. 99-102.

DiPaolo, 1963, "In vitro Test Systems for Cancer Chemotherapy, II. Correlation of in vitro Inhibition of Dehydrogenase and Growth with in vivo Inhibition of Ehrlich Asoites Tumor," *Proceedings of the Society for Experimental Biology & Medicine* 114:384-387.

Dredge et al., 2002, "Novel thalidomide analogues display antiangiogenic activity independently of immunomodulatory effects," Br. J. Cancer 87(10):1166-1172.

Eisen et al., 2000, "Continuous low dose Thalidomide: a phase II study in advanced melanoma, renal cell, ovarian and breast cancer," Br. J. Cancer 82(4):812-817.

Emens et al., 2001, "Chemotherapy: friend or foe to cancer vaccines?" Curr. Opin. Mol. Ther. 3(1):77-84.

Fakhouri et al., 2004, "Thalidomide in patients with multiple myeloma and renal failure," Br. J. Haematol. 125:90-102.

Fenk et al., 2005, "Single-agent thalidomide for treatment of first relapse following high-dose chemotherapy in patients with multiple myeloma," Leukemia 19(1):156-159.

Folkman et al., 1983, "Angiogenesis inhibition and tumor regression caused by heparin or a heparin fragment in the presence of cortisone," Science 221(4612):719-725.

Gershbein, 1991, "The thalidomide analog, EM 12, enhances 1,2-dimethylhydrazine-induction of rat colon adenocarcinomas," Cancer Letters 60: 129-133.

Grabstald et al., 1965, "Clinical experiences with thalidomide in patients with cancer," Clinical Pharmacology and Therapeutics 6:298-302.

Gupta et al., 2001, "Adherence of multiple myeloma cells to bone marrow stromal cells upregulates vascular endothelial growth factor secretion: therapeutic applications," Leukemia 15(12):1950-1961.

Haslett et al., 2003, "Thalidomide and a thalidomide analogue drug costimulate virus-specific CD8+ T cells in vitro," J. Infect. Dis. 187(6):946-955.

He, W., et al., 1993, Abstract of papers, 206th American Chemical Society, Chicago, IL; Med. Chem., paper 216.

Hideshima et al., 2000, "Thalidomide and its analogs overcome drug resistance of human multiple myeloma cells to conventional therapy," Blood 96(9):2943-2950.

Jonsson, 1972, "Chemical Structure and Teratogenic Properties," Acta Pharm., pp. 521-542.

Lentzsch et al., 2003, "Immunomodulatory analogs of thalidomide inhibit growth of Hs Sultan cells and angiogenesis in vivo," Leukemia 17(1):41-44.

Lentzsch et al., 2002, "S-3-amino-phthalimido-glutarimide inhibits angiogenesis and growth of B-cell neoplasias in mice," Cancer Research 62:2300-2305.

Mauad, 1963, "Clinical Improvements Obtained in Advanced Caner Patients with Treatment with Thalidomide Associated with Hormones," Anais *Paulistas de Medicina e Cirurgia*, 86:13-40.

Miyachi et al., 1997, "Novel biological response modifiers; phthalimides with tumor necrosis factor-alpha production-regulating activity," J. Med. Chem. 40:2858-2865.

Muckter, 1966, "Thalidomide and Tumor," Antimicrobial Agents and Chemotherapy pp. 531-538.

Muller et al., 1999, "Amino-substituted thalidomide analogs: potent inhibitors of TNF-alpha production," Bioorg. Med. Chem. Lett. 9(11):1625-1630.

Muller et al., 1998, "Thalidomide analogs and PDE4 inhibition," Bioorg. Med. Chem. Lett. 8(19):2669-2674.

Muller et al., 1996, "Structural modifications of thalidomide produce analogs with analogs with enhanced tumor necrosis factor inhibitory activity," J. Med. Chem. 39(17):3238-3240.

Offidani et al., 2003, "Thalidomide plus oral melphalan for advanced multiple myeloma: a phase II study," Haematologica 88(12):1432-1433.

Olson et al., 1965, "Thalidomide (N-phthaloylglutamimide) in the treatment of advanced cancer," Clinical Pharmacology and Therapeutics 6(3):292-297.

Palumbo et al., 2004, "A prospective randomized trial of oral melphalan prednisone, thalidomide (MPT) vs. oral melphalan, prednisone (MP): An interim analysis," Am. Soc. Hematol. 46th Ann. Meeting Dec. 4-7, 2004, San Diego, CA Abstract #207.

Penichet et al., 2001, "Antibody-cytokine fusion proteins for the therapy of cancer,"J. Immunol. Methods 248(1-2):91-101.

Physicians' Desk Ref. 2002, 56th ed., pp. 1755-1760.

Raje et al., 1999, "Thalidomide—a revival story," N. Engl. J. Med. 341(21):1606-1609.

Rajkumar et al., 2004, "Thalidomide plus dexamethasone versus dexamethasone alone in newly diagnosed multiple myeloma (E1A00): Results of a phase III trial coordinated by the Eastern Cooperative Oncology Group," Am. Soc. Hematol. 46th Ann. Meeting Dec. 4-7, 2004, San Diego, CA Abstract #205.

Rajkumar et al., 2000, "Prognostic value of bone marrow angiogenesis in multiple myeloma," Clin. Cancer Res. 6(8):3111-3116.

Raza et al., 2001, "Thalidomide produces transfusion independence in long-standing refractory anemias of patients with myelodysplatic syndromes," Blood 98(4):958-965.

Ribatti et al., 1999, "Bone marrow angiogenesis and mast cell density increase simultaneously with progression of human multiple myeloma," Br. J. Cancer 79(3-4):451-455.

Roe et al., 1963, "Thalidomide and Neoplasia," *Nature*, Dec. 7, 200:1016-17.

Shah et al., 1999, "Synthesis and enantiomeric separation of 2-phthalimidino-glutaric acid analogues: potent inhibitors of tumor metastasis," J. Med. Chem. 42:3014-3017.

Shibata et al., 1995, "N-alkylphthalimides: structural requirement of thalidomidal action on 12-0-tetradecanoylphorbol-13-acetate-induced tumor necrosis factor a production by human leukemia HL-60 cells," Chem. Pharm. Bull. 43(1):177-179.

Shimazawa et al., 1999, "Antiangiogenic activity of tumor necrosis factor-alpha production regulators derived from thalidomide," Biol. Pharm. Bull. 22(2):224-226.

Singhal et al., 1999, "Antitumor activity of thalidomide in refractory multiple myeloma," N. Engl. J. Med. 341(21):1565-1571.

Steins et al., 2002, "Efficacy and safety of thalidomide in patients with acute myeloid leukemia," Blood 99(3):834-839.

Stockdale, 1998, *Medicine*, Rubenstein and Federman, eds., vol. 3, Ch. 12, Sections IV and X.

Sugiura et al., 1964, "Effect of thalidomide on transplantable mouse, rat, and hamster tumors," Gann. 55:57-60.

Vacca et al., 1999, "Bone marrow neovascularization, plasma cell angiogenic potential, and matrix metalloproteinase-2 secretion parallel progression of human multiple myeloma," Blood 93(9):3064-3073.

Wohrer et al., 2004, "Effective treatment of primary plasma cell leukemia with thalidomide and dexamethasone—a case report," Hematol. J. 5:361-363.

Wolff, ed., 1995, 1 Burger's Medicinal Chemistry and Drug Discovery, 5th ed., 172-178, 949-982.

Baatz, H.; Tonessen, B.; Prada, J.; Pleyer, U.;Thalidomide Inhibits Leukocyte-Endothelium Interaction in Endotoxin-Induced Uveitis, Opthalmic Research, 2001;33:256-263.

METHODS FOR TREATMENT OF CHRONIC UVEITIS USING CYCLOPROPYL-N-{2-[(1S)-1-(3-ETHOXY-4-METHOXYPHENYL)-2-(METHYLSULFONYL) ETHYL]-3-OXOISOINDOLINE-4-YL} CARBOXAMIDE

This application claims the benefit of U.S. provisional application No. 60/424,601, filed Nov. 6, 2002, the entirety of which is incorporated herein by reference.

1. FIELD OF THE INVENTION

This invention relates to methods of treating, preventing and/or managing specific cancers, and other diseases including, but not limited to, those associated with, or characterized by, undesired angiogenesis, by the administration of one or more selective cytokine inhibitory drugs alone or in combination with other therapeutics. In particular, the invention encompasses the use of specific combinations, or "cocktails," of drugs and other therapy, e.g., radiation to treat these specific cancers, including those refractory to conventional therapy. The invention also relates to pharmaceutical compositions and dosing regimens.

2. BACKGROUND OF THE INVENTION

2.1. Pathobiology of Cancer and Other Diseases

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis, Mo., 1993).

There is an enormous variety of cancers which are described in detail in the medical literature. Examples includes cancer of the lung, colon, rectum, prostate, breast, brain, and intestine. The incidence of cancer continues to climb as the general population ages, as new cancers develop, and as susceptible populations (e.g., people infected with AIDS or excessively exposed to sunlight) grow. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g. TNF-α, bFGF).

A variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, and autoimmune diseases. Examples of such diseases and conditions include, but are not limited to: diabetic retinopathy; retinopathy of prematurity; corneal graft rejection; neovascular glaucoma; retrolental fibroplasia; and proliferative vitreoretinopathy.

Accordingly, compounds that can control angiogenesis or inhibit the production of certain cytokines, including TNF-α, may be useful in the treatment and prevention of various diseases and conditions.

2.2. Methods of Treatment

Current cancer therapy may involve surgery, chemotherapy, hormonal therapy and/or radiation treatment to eradicate neoplastic cells in a patient (see, for example, Stockdale, 1998, *Medicine*, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Biological therapies and immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A majority of cancer chemotherapeutics act by inhibiting DNA synthesis, either directly, or indirectly by inhibiting the biosynthesis of deoxyribonucleotide triphosphate precursors, to prevent DNA replication and concomitant cell division. Gilman et al., *Goodman and Gilman's: The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance.

Because of the drug resistance, many cancers prove refractory to standard chemotherapeutic treatment protocols.

Other diseases or conditions associated with, or characterized by, undesired angiogenesis are also difficult to treat. However, some compounds such as protamine, hepain and steroids have been proposed to be useful in the treatment of certain specific diseases. Taylor et al., *Nature* 297:307 (1982); Folkman et al., *Science* 221:719 (1983); and U.S. Pat. Nos. 5,001,116 and 4,994,443. Thalidomide and certain derivatives of it have also been proposed for the treatment of such diseases and conditions. U.S. Pat. Nos. 5,593,990, 5,629,327, 5,712,291, 6,071,948 and 6,114,355 to D'Amato.

Still, there is a significant need for safe and effective methods of treating, preventing and managing cancer and other diseases and conditions, particularly for diseases that are refractory to standard treatments, such as surgery, radiation therapy, chemotherapy and hormonal therapy, while reducing or avoiding the toxicities and/or side effects associated with the conventional therapies.

2.3. Selective Cytokine Inhibitory Drugs

Compounds referred to as SelCIDs™ (Celgene Corporation) or Selective Cytokine Inhibitory Drugs have been synthesized and tested. These compounds potently inhibit TNF-α production, but exhibit modest inhibitory effects on LPS induced IL1β and IL12, and do not inhibit IL6 even at high drug concentrations. In addition, SelCIDs™ tend to produce a modest IL10 stimulation. L. G. Corral, et al., Ann. Rheum. Dis. 58:(Suppl I) 1107-1113 (1999).

Further characterization of the selective cytokine inhibitory drugs shows that they are potent PDE4 inhibitors. PDE4 is one of the major phosphodiesterase isoenzymes found in human myeloid and lymphoid lineage cells. The enzyme plays a crucial part in regulating cellular activity by degrading the ubiquitous second messenger cAMP and maintaining it at low intracellular levels. Id. Inhibition of PDE4 activity results in increased cAMP levels leading to the modulation of LPS induced cytokines including inhibition of TNF-α production in monocytes as well as in lymphocytes.

3. SUMMARY OF THE INVENTION

This invention encompasses methods of treating and preventing certain types of cancer, including primary and metastatic cancer, as well as cancers that are refractory or resistant to conventional chemotherapy. The methods comprise administering to a patient in need of such treatment or prevention a therapeutically or prophylactically effective amount of a selective cytokine inhibitory drug, or a pharmaceutically acceptable salt, solvate, hydrate, stereoisomer, clathrate, or prodrug thereof. The invention also encompasses methods of managing certain cancers (e.g., preventing or prolonging their recurrence, or lengthening the time of remission) which comprise administering to a patient in need of such management a prophylactically effective amount of a selective cytokine inhibitory drug of the invention, or a pharmaceutically acceptable salt, solvate, hydrate, stereoisomer, clathrate, or prodrug thereof.

In particular methods of the invention, a selective cytokine inhibitory drug is administered in combination with a therapy conventionally used to treat, prevent or manage cancer. Examples of such conventional therapies include, but are not limited to, surgery, chemotherapy, radiation therapy, hormonal therapy, biological therapy and immunotherapy.

This invention also encompasses methods of treating, managing or preventing diseases and disorders other than cancer that are associated with, or characterized by, undesired angiogenesis, which comprise administering to a patient in need of such treatment, management or prevention a therapeutically or prophylactically effective amount of a selective cytokine inhibitory drug, or a pharmaceutically acceptable salt, solvate, hydrate, stereoisomer, clathrate, or prodrug thereof.

In other methods of the invention, a selective cytokine inhibitory drug is administered in combination with a therapy conventionally used to treat, prevent or manage diseases or disorders associated with, or characterized by, undesired angiogenesis. Examples of such conventional therapies include, but are not limited to, surgery, chemotherapy, radiation therapy, hormonal therapy, biological therapy and immunotherapy.

This invention encompasses pharmaceutical compositions, single unit dosage forms, dosing regimens and kits which comprise a selective cytokine inhibitory drug, or a pharmaceutically acceptable salt, solvate, hydrate, stereoisomer, clathrate, or prodrug thereof, and a second, or additional, active agent. Second active agents include specific combinations, or "cocktails," of drugs.

4. DETAILED DESCRIPTION OF THE INVENTION

A first embodiment of the invention encompasses methods of treating, managing, or preventing cancer which comprises administering to a patient in need of such treatment or prevention a therapeutically or prophylactically effective amount of a selective cytokine inhibitory drug of the invention, or a pharmaceutically acceptable salt, solvate, hydrate, stereoisomer, clathrate, or prodrug thereof.

In particular methods encompassed by this embodiment, the selective cytokine inhibitory drug is administered in combination with another drug ("second active agent") or method of treating, managing, or preventing cancer. Second active agents include small molecules and large molecules (e.g., proteins and antibodies), examples of which are provided herein, as well as stem cells. Methods, or therapies, that can be used in combination with the administration of the selective cytokine inhibitory drug include, but are not limited to, surgery, blood transfusions, immunotherapy, biological therapy, radiation therapy, and other non-drug based therapies presently used to treat, prevent or manage cancer.

Another embodiment of the invention encompasses methods of treating, managing or preventing diseases and disorders other than cancer that are characterized by undesired angiogenesis. These methods comprise the administration of a therapeutically or prophylactically effective amount of a selective cytokine inhibitory drug, or a pharmaceutically acceptable salt, solvate, hydrate, stereoisomer, clathrate, or prodrug thereof.

Examples of diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, and rubeosis (neovascularization of the angle).

In particular methods encompassed by this embodiment, the selective cytokine inhibitory drug is administer in combination with a second active agent or method of treating, managing, or preventing the disease or condition. Second active agents include small molecules and large molecules (e.g., proteins and antibodies), examples of which are provided herein, as well as stem cells. Methods, or therapies, that can be used in combination with the administration of the selective cytokine inhibitory drug include, but are not limited to, surgery, blood transfusions, immunotherapy, biological therapy, radiation therapy, and other non-drug based therapies presently used to treat, prevent or manage disease and conditions associated with, or characterized by, undesired angiogenesis.

The invention also encompasses pharmaceutical compositions (e.g., single unit dosage forms) that can be used in methods disclosed herein. Particular pharmaceutical compositions comprise a selective cytokine inhibitory drug of the invention, or a pharmaceutically acceptable salt, solvate, hydrate, stereoisomer, clathrate, or prodrug thereof, and a second active agent.

4.1. Selective Cytokine Inhibitory Drugs

Compounds used in the invention include racemic, stereomerically pure and stereomerically enriched selective cytokine inhibitory drugs, stereomerically and enantiomerically pure compounds that have selective cytokine inhibitory activities, and pharmaceutically acceptable salts, solvates, hydrates, stereoisomers, clathrates, and prodrugs thereof. Preferred compounds used in the invention are known Selective Cytokine Inhibitory Drugs (SelCIDs™) of Celgene Corporation, NJ.

As used herein and unless otherwise indicated, the terms "selective cytokine inhibitory drugs" and "SelCIDs™" encompass small molecule drugs, e.g., small organic molecules which are not peptides, proteins, nucleic acids, oligosaccharides or other macromolecules. Preferred compounds inhibit TNF-α production. Compounds may also have a modest inhibitory effect on LPS induced IL1β and IL12. More preferably, the compounds of the invention are potent PDE4 inhibitors.

Specific examples of selective cytokine inhibitory drugs include, but are not limited to, the cyclic imides disclosed in U.S. Pat. Nos. 5,605,914 and 5,463,063; the cycloalkyl amides and cycloalkyl nitriles of U.S. Pat. Nos. 5,728,844, 5,728,845, 5,968,945, 6,180,644 and 6,518,281; the aryl amides (for example, an embodiment being N-benzoyl-3-amino-3-(3',4'-dimethoxyphenyl)-propanamide) of U.S. Pat. Nos. 5,801,195, 5,736,570, 6,046,221 and 6,284,780; the imide/amide ethers and alcohols (for example, 3-phthalimido-3-(3',4'-diimethoxyphenyl)propan-1-ol) disclosed in U.S. Pat. No. 5,703,098; the succinimides and maleimides (for example methyl 3-(3',4',5',6'-petrahydrophthalimdo)-3-(3",4"-dimethoxyphenyl)propionate) disclosed in U.S. Pat. No. 5,658,940; imido and amido substituted alkanohydroxamic acids disclosed in U.S. Pat. No. 6,214,857 and WO 99/06041; substituted phenethylsulfones disclosed in U.S. Pat. Nos. 6,011,050 and 6,020,358; substituted imides (for example, 2-phthalimido-3-(3',4'-dimethoxyphenyl)propane) disclosed in U.S. Pat. No. 6,429,221; substituted 1,3,4-oxadiazoles (for example, 2-[1-(3-cyclopentyloxy-4-methoxyphenyl)-2-(1,3,4-oxadiazole-2-yl)ethyl]-5-methylisoindoline-1,3-dione) disclosed in U.S. Pat. No. 6,326,388; cyano and carboxy derivatives of substituted styrenes (for example, 3,3-bis-(3,4-dimethoxyphenyl)acrylonitrile) disclosed in U.S. Pat. Nos. 5,929,117, 6,130,226, 6,262,101 and 6,479,554; isoindoline-1-one and isoindoline-1,3-dione substituted in the 2-position with an α-(3,4-disubstituted phenyl)alkyl group and in the 4- and/or 5-position with a nitrogen-containing group disclosed in WO 01/34606; and imido and amido substituted acylhydroxamic acids (for example, (3-(1,3-dioxoisoindoline-2-yl)-3-(3-ethoxy-4-methoxyphenyl)propanoylamino) propanoate disclosed in WO 01/45702. The entireties of each of the patents and patent applications identified herein are incorporated herein by reference.

Additional selective cytokine inhibitory drugs belong to a family of synthesized chemical compounds of which typical embodiments include 3-(1,3-dioxobenzo-[f]isoindol-2-yl)-3-(3-cyclopentyloxy-4-methoxyphenyl)propionamide and 3-(1,3-dioxo-4-azaisoindol-2-yl)-3-(3,4-dimethoxyphenyl)-propionamide.

Other specific selective cytokine inhibitory drugs belong to a class of non-polypeptide cyclic amides disclosed in U.S. Pat. Nos. 5,698,579, 5,877,200, 6,075,041 and 6,200,987, each of which is incorporated herein. Representative cyclic amides include compounds of the formula:

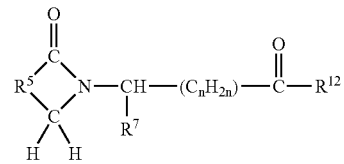

wherein n has a value of 1, 2, or 3;

$R^5$ is o-phenylene, unsubstituted or substituted with 1 to 4 substituents each selected independently from the group consisting of nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkyl of 1 to 10 carbon atoms, and halo;

$R^7$ is (i) phenyl or phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo, (ii) benzyl unsubstituted or substituted with 1 to 3 substituents selected from the group consisting of nitro, cyano, trifluoromethyl, carbothoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo, (iii) naphthyl, and (iv) benzyloxy;

$R^{12}$ is —OH, alkoxy of 1 to 12 carbon atoms, or

$R^8$ is hydrogen or alkyl of 1 to 10 carbon atoms; and
$R^9$ is hydrogen, alkyl of 1 to 10 carbon atoms, —COR$^{10}$, or —SO$_2$R$^{10}$, wherein R$^{10}$ is hydrogen, alkyl of 1 to 10 carbon atoms, or phenyl.

Specific compounds of this class include, but are not limited to:
3-phenyl-2-(1-oxoisoindolin-2-yl)propionic acid;
3-phenyl-2-(1-oxoisoindolin-2-yl)propionamide;
3-phenyl-3-(1-oxoisoindolin-2-yl)propionic acid;
3-phenyl-3-(1-oxoisoindolin-2-yl)propionamide;
3-(4-methoxyphenyl)-3-(1-oxisoindolin-yl)propionic acid;
3-(4-methoxyphenyl)-3-(1-oxisoindolin-yl)propionamide;

3-(3,4-dimethoxyphenyl)-3-(1-oxisoindolin-2-yl)propionic acid;
3-(3,4-dimethoxy-phenyl)-3-(1-oxo-1,3-dihydroisoindol-2-yl)propionamide;
3-(3,4-dimethoxyphenyl)-3-(1-oxisoindolin-2-yl)propionamide;
3-(3,4-diethoxyphenyl)-3-(1-oxoisoindolin-yl)propionic acid;
methyl 3-(1-oxoisoindolin-2-yl)-3-(3-ethoxy-4-methoxyphenyl)propionate;
3-(1-oxoisoindolin-2-yl)-3-(3-ethoxy-4-methoxyphenyl)propionic acid;
3-(1-oxoisoindolin-2-yl)-3-(3-propoxy-4-methoxyphenyl)propionic acid;
3-(1-oxoisoindolin-2-yl)-3-(3-butoxy-4-methoxyphenyl)propionic acid;
3-(1-oxoisoindolin-2-yl)-3-(3-propoxy-4-methoxyphenyl)propionamide;
3-(1-oxoisoindolin-2-yl)-3-(3-butoxy-4-methoxyphenyl)propionamide;
methyl 3-(1-oxoisoindolin-2-yl)-3-(3-butoxy-4-methoxyphenyl)propionate; and
methyl 3-(1-oxoisoindolin-2-yl)-3-(3-propoxy-4-methoxyphenyl)propionate. Other representative cyclic amides include compounds of the formula:

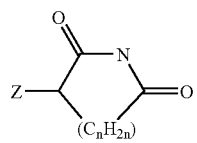

in which Z is:

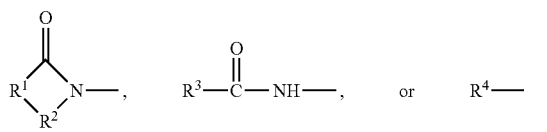

in which:
$R^1$ is the divalent residue of (i) 3,4-pyridine, (ii) pyrrolidine, (iii) imidizole, (iv) naphthalene, (v) thiophene, or (vi) a straight or branched alkane of 2 to 6 carbon atoms, unsubstituted or substituted with phenyl or phenyl substituted with nitro, cyano, trifluoromethyl, carbethoxy, carbomethoxy, carbopropoxy, acetyl, carbamyl, acetoxy, carboxy, hydroxy, amino, alkyl of 1 to 10 carbon atoms, alkoxy of 1 to 10 carbon atoms, or halo, wherein the divalent bonds of said residue are on vicinal ring carbon atoms;
$R^2$ is —CO— or —SO$_2$—;
$R^3$ is (i) phenyl substituted with 1 to 3 substituents each selected independently from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, (ii) pyridyl, (iii) pyrrolyl, (iv) imidazolyl, (iv) naphthyl, (vi) thienyl, (vii) quinolyl, (viii) furyl, or (ix) indolyl;
$R^4$ is alanyl, arginyl, glycyl, phenylglycyl, histidyl, leucyl, isoleucyl, lysyl, methionyl, prolyl, sarcosyl, seryl, homoseryl, threonyl, thyronyl, tyrosyl, valyl, benzimidol-2-yl, benzoxazol-2-yl, phenylsulfonyl, methylphenylsulfonyl, or phenylcarbamoyl; and n has a value of 1, 2, or 3. Other representative cyclic amides include compounds of the formula:

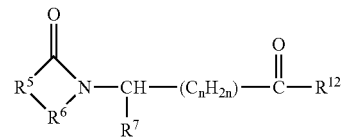

in which $R^5$ is (i) o-phenylene, unsubstituted or substituted with 1 to 4 substituents each selected independently from nitro, cyano, trifluoromethyl, carbethoxy, carbomethoxy, carbopropoxy, acetyl, carbamoyl, acetoxy, carboxy, hydroxy, amino, akylamino, dialkylamino, acylamino, alkyl of 1 to 10 carbon atoms, alkoxy of 1 to 10 carbon atoms, or halo, or (ii) the divalent residue of pyridine, pyrrolidine, imidizole, naphthalene, or thiophene, wherein the divalent bonds are on vicinal ring carbon atoms;
$R^6$ is —CO—, —CH$_2$—, or —SO$_2$—;
$R^7$ is (i) hydrogen if $R^6$ is —SO$_2$—, (ii) straight, branched, or cyclic alkyl of 1 to 12 carbon atoms, (iii) pyridyl, (iv) phenyl or phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, (v) alkyl of 1 to 10 carbon atoms, (vi) benzyl unsubstituted or substituted with 1 to 3 substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, (vii) naphthyl, (viii) benzyloxy, or (ix) imidazol-4-yl methyl;
$R^{12}$ is —OH, alkoxy of 1 to 12 carbon atoms, or

n has a value of 0, 1, 2, or 3;
R8' is hydrogen or alkyl of 1 to 10 carbon atoms; and
$R^{9'}$ is hydrogen, alkyl of 1 to 10 carbon atoms, —COR$^{10}$, or —SO$_2$R$^{10}$ in which R$^{10}$ is hydrogen, alkyl of 1 to 10 carbon atoms, or phenyl.

Other specific selective cytokine inhibitory drugs include the imido and amido substituted alkanohydroxamic acids disclosed in WO 99/06041, which is incorporated herein by reference. Examples of such compound include, but are not limited to:

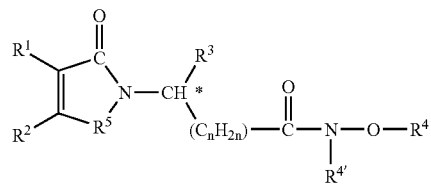

wherein each of $R^1$ and $R^2$, when taken independently of each other, is hydrogen, lower alkyl, or $R^1$ and $R^2$, when taken together with the depicted carbon atoms to which each is bound, is o-phenylene, o-naphthylene, or cyclohexene-1, 2-diyl, unsubstituted or substituted with 1 to 4 substituents each selected independently from the group consisting of nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkoxy of 1 to 10 carbon atoms, and halo;

$R^3$ is phenyl substituted with from one to four substituents selected from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, alkylthio of 1 to 10 carbon atoms, benzyloxy, cycloalkoxy of 3 to 6 carbon atoms, $C_4$-$C_6$-cycloalkylidenemethyl, $C_3$-$C_{10}$-alkylidenemethyl, indanyloxy, and halo;

$R^4$ is hydrogen, alkyl of 1 to 6 carbon atoms, phenyl, or benzyl;

$R^{4'}$ is hydrogen or alkyl of 1 to 6 carbon atoms;

$R^5$ is —$CH_2$—, —$CH_2$—CO—, —$SO_2$—, —S—, or —NHCO—;

n has a value of 0, 1, or 2; and the acid addition salts of said compounds which contain a nitrogen atom capable of being protonated.

Additional specific selective cytokine inhibitory drugs used in the invention include, out are not limited to:

3-(3-ethoxy-4-methoxyphenyl)-N-hydroxy-3-(1-oxoisoindolinyl)propionamide;
3-(3-ethoxy-4-methoxyphenyl)-N-methoxy-3-(1-oxoisoindolinyl)propionamide;
N-benzyloxy-3-(3-ethoxy-4-methoxyphenyl)-3-phthalimidopropionamide;
N-benzyloxy-3-(3-ethoxy-4-methoxyphenyl)-3-(3-nitrophthalimido)propionamide;
N-benzyloxy-3-(3-ethoxy-4-methoxyphenyl)-3-(1-oxoisoindolinyl)propionamide;
3-(3-ethoxy-4-methoxyphenyl)-N-hydroxy-3-phthalimidopropionamide;
N-hydroxy-3-(3,4-dimethoxyphenyl)-3-phthalimidopropionamide;
3-(3-ethoxy-4-methoxyphenyl)-N-hydroxy-3-(3-nitrophthalimido)propionamide;
N-hydroxy-3-(3,4-dimethoxyphenyl)-3-(1-oxoisoindolinyl)propionamide;
3-(3-ethoxy-4-methoxyphenyl)-N-hydroxy-3-(4-methyl-phthalimido)propionamide;
3-(3-cyclopentyloxy-4-methoxyphenyl)-N-hydroxy-3-phthalimidopropionamide;
3-(3-ethoxy-4-methoxyphenyl)-N-hydroxy-3-(1,3-dioxo-2,3-dihydro-1H-benzo[f]isoindol-2-yl)propionamide;
N-hydroxy-3-{3-(2-propoxy)-4-methoxyphenyl}-3-phthalimidopropionamide;
3-(3-ethoxy-4-methoxyphenyl)-3-(3,6-difluorophthalimido)-N-hydroxypropionamide;
3-(4-aminophthalimido)-3-(3-ethoxy-4-methoxyphenyl)-N-hydroxypropionamide;
3-(3-aminophthalimido)-3-(3-ethoxy-4-methoxyphenyl)-N-hydroxypropionamide;
N-hydroxy-3-(3,4-dimethoxyphenyl)-3-(1-oxoisoindolinyl)propionamide;
3-(3-cyclopentyloxy-4-methoxyphenyl)-N-hydroxy-3-(1-oxoisoindolinyl) propionamide; and
N-benzyloxy-3-(3-ethoxy-4-methoxyphenyl)-3-(3-nitrophthalimido)propionamide.

Additional selective cytokine inhibitory drugs used in the invention include the substituted phenethylsulfones substituted on the phenyl group with a oxoisoindine group. Examples of such compounds include, but are not limited to, those disclosed in U.S. Pat. No. 6,020,358, which is incorporated herein, which include the following:

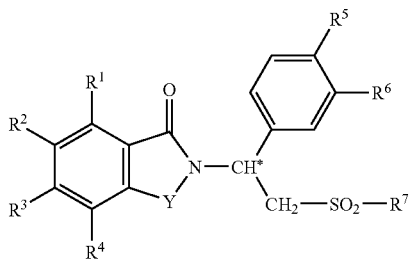

wherein the carbon atom designated * constitutes a center of chirality;

Y is C=O, $CH_2$, $SO_2$, or $CH_2$C=O; each of $R^1$, $R^2$, $R^3$, and $R^4$, independently of the others, is hydrogen, halo, alkyl of 1 to 4 carbon atoms, alkoxy of 1 to 4 carbon atoms, nitro, cyano, hydroxy, or —$NR^8R^9$; or any two of $R^1$, $R^2$, $R^3$, and $R^4$ on adjacent carbon atoms, together with the depicted phenylene ring are naphthylidene;

each of $R^5$ and $R^6$, independently of the other, is hydrogen, alkyl of 1 to 4 carbon atoms, alkoxy of 1 to 4 carbon atoms, cyano, or cycloalkoxy of up to 18 carbon atoms;

$R^7$ is hydroxy, alkyl of 1 to 8 carbon atoms, phenyl, benzyl, or $NR^8R^{9'}$;

each of $R^8$ and $R^9$ taken independently of the other is hydrogen, alkyl of 1 to 8 carbon atoms, phenyl, or benzyl, or one of $R^8$ and $R^9$ is hydrogen and the other is —$COR^{10}$ or —$SO_2R^{10}$, or $R^8$ and $R^9$ taken together are tetramethylene, pentamethylene, hexamethylene, or —$CH_2CH_2X^1CH_2CH_2$— in which $X^1$ is —O—, —S— or —NH—; and each of $R^{8'}$ and $R^{9'}$ taken independently of the other is hydrogen, alkyl of 1 to 8 carbon atoms, phenyl, or benzyl, or one of $R^{8'}$ and $R^{9'}$ is hydrogen and the other is —$COR^{10'}$ or —$SO_2R^{10'}$, or $R^{8'}$ and $R^{9'}$ taken together are tetramethylene, pentamethylene, hexamethylene, or —$CH_2CH_2X^2CH_2CH_2$— in which $X^2$ is —O—, —S—, or —NH—.

It will be appreciated that while for convenience the above compounds are identified as phenethylsulfones, they include sulfonamides when $R^7$ is $NR^8R^{9'}$.

Specific groups of such compounds are those in which Y is C=O or $CH_2$.

A further specific group of such compounds are those in which each of $R^1$, $R^2$, $R^3$, and $R^4$ independently of the others, is hydrogen, halo, methyl, ethyl, methoxy, ethoxy, nitro, cyano, hydroxy, or —$NR^8R^9$ in which each of $R^8$ and $R^9$ taken independently of the other is hydrogen or methyl or one of $R^8$ and $R^9$ is hydrogen and the other is —$COCH_3$.

Particular compounds are those in which one of $R^1$, $R^2$, $R^3$, and $R^4$ is —$NH_2$ and the remaining of $R^1$, $R^2$, $R^3$, and $R^4$ are hydrogen.

Particular compounds are those in which one of $R^1$, $R^2$, $R^3$, and $R^4$ is —$NHCOCH_3$ and the remaining of $R^1$, $R^2$, $R^3$, and $R^4$ are hydrogen.

Particular compounds are those in which one of $R^1$, $R^2$, $R^3$, and $R^4$ is —$N(CH_3)_2$ and the remaining of $R^1$, $R^2$, $R^3$, and $R^4$ are hydrogen.

A further preferred group of such compounds are those in which one of $R^1$, $R^2$, $R^3$, and $R^4$ is methyl and the remaining of $R^1$, $R^2$, $R^3$, and $R^4$ are hydrogen.

Particular compounds are those in which one of $R^1$, $R^2$, $R^3$, and $R^4$ is fluoro and the remaining of $R^1$, $R^2$, $R^3$, and $R^4$ are hydrogen.

Particular compounds are those in which each of $R^5$ and $R^6$, independently of the other, is hydrogen, methyl, ethyl, propyl, methoxy, ethoxy, propoxy, cyclopentoxy, or cyclohexoxy.

Particular compounds are those in which $R^5$ is methoxy and $R^6$ is monocycloalkoxy, polycycloalkoxy, and benzocycloalkoxy.

Particular compounds are those in which $R^5$ is methoxy and $R^6$ is ethoxy.

Particular compounds are those in which $R^7$ is hydroxy, methyl, ethyl, phenyl, benzyl, or $NR^{8'}R^{9'}$ in which each of $R^{8'}$ and $R^{9'}$ taken independently of the other is hydrogen or methyl.

Particular compounds are those in which $R^7$ is methyl, ethyl, phenyl, benzyl or $NR^{8'}R^{9'}$ in which each of $R^{8'}$ and $R^{9'}$ taken independently of the other is hydrogen or methyl.

Particular compounds are those in which $R^7$ is methyl.

Particular compounds are those in which $R^7$ is $NR^{8'}R^{9'}$ in which each of $R^{8'}$ and $R^{9'}$ taken independently of the other is hydrogen or methyl.

Additional selective cytokine inhibitory drugs include the enantiomerically pure compounds disclosed in U.S. patent application Ser. No. 10/392,195 filed on Mar. 19, 2003; international patent application nos. PCT/US03/08737 and PCT/US03/08738, filed on Mar. 20, 2003; U.S. provisional patent application Nos. 60/438,450 and 60/438,448 to G. Muller et al., both of which were filed on Jan. 7, 2003; and U.S. provisional patent application No. 60/452,460 to G. Muller et al. filed on Mar. 5, 2003, all of which are incorporated herein by reference. Preferred compounds include an enantiomer of 2-[1-(3-ethoxy-4-methoxyphenyl)-2-methylsulfonylethyl]-4-acetylaminoisoindoline-1,3-dione and an enantiomer of 3-(3,4-dimethoxy-phenyl)-3-(1-oxo-1,3-dihydro-isoindol-2-yl)-propionamide.

Preferred selective cytokine inhibitory drugs used in the invention are 3-(3,4-dimethoxy-phenyl)-3-(1-oxo-1,3-dihydro-isoindol-2-yl)-propionamide and cyclopropanecarboxylic acid {2-[1-(3-ethoxy-4-methoxy-phenyl)-2-methanesulfonyl-ethyl]-3-oxo-2,3-dihydro-1H-isoindol-4-yl}-amide, which are available from Celgene Corp., Warren, N.J. 3-(3,4-Dimethoxy-phenyl)-3-(1-oxo-1,3-dihydro-isoindol-2-yl)-propionamide has the following chemical structure:

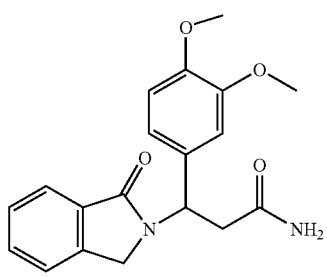

Other specific selective cytokine inhibitory drugs include, but are not limited to, the cycloalkyl amides and cycloalkyl nitriles of U.S. Pat. Nos. 5,728,844, 5,728,845, 5,968,945, 6,180,644 and 6,518,281, each of which is incorporated herein by reference.

Representative compounds are of formula:

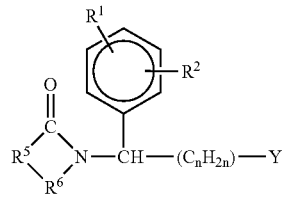

wherein:
one of $R^1$ and $R^2$ is $R^3$—X— and the other is hydrogen, nitro, cyano, trifluoromethyl, carbo(lower)alkoxy, acetyl, carbamoyl, acetoxy, carboxy, hydroxy, amino, lower alkyl, lower alkoxy, halo, or $R^3$—X—;

$R^3$ is monocycloalkyl, bicycloalkyl, benzocycloalkyl of up to 18 carbon atoms;

X is a carbon-carbon bond, —$CH_2$—, or —O—;

$R^5$ is (i) o-phenylene, unsubstituted or substituted with 1 to 3 substituents each selected independently from nitro, cyano, halo, trifluoromethyl, carbo(lower)alkoxy, acetyl, or carbamoyl, unsubstituted or substituted with lower alkyl, acetoxy, carboxy, hydroxy, amino, lower alkylamino, lower acylamino, or lower alkoxy; (ii) a vicinally divalent residue of pyridine, pyrrolidine, imidazole, naphthalene, or thiophene, wherein the divalent bonds are on vicinal ring carbon atoms; (iii) a vicinally divalent cycloalkyl or cycloalkenyl of 4-10 carbon atoms, unsubstituted or substituted with 1 to 3 substituents each selected independently from the group consisting of nitro, cyano, halo, trifluoromethyl, carbo(lower)alkoxy, acetyl, carbamoyl, acetoxy, carboxy, hydroxy, amino, lower alkylamino, lower alkyl, lower alkoxy, or phenyl; (iv) vinylene di-substituted with lower alkyl; or (v) ethylene, unsubstituted or monosubstituted or disubstituted with lower alkyl;

$R^6$ is —CO—, —$CH_2$—, or —$CH_2CO$—;

Y is —COZ, —C≡N, —$OR^8$, lower alkyl, or aryl;

Z is —$NH_2$, —OH, —NHR, —$R^9$, or —$OR^9$ $R^8$ is hydrogen or lower alkyl;

$R^9$ is lower alkyl or benzyl; and, n has a value of 0, 1, 2, or 3. Other representative compounds are of formula:

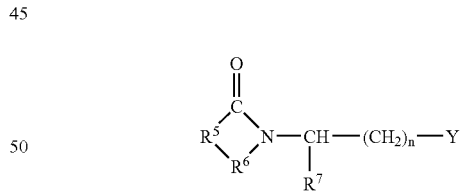

wherein:
Y is —C≡N or $CO(CH_2)_mCH_3$;

m is 0, 1, 2, or 3;

$R^5$ is (i) o-phenylene, unsubstituted or substituted with 1 to 3 substituents each selected independently from nitro, cyano, trifluoromethyl, carbethoxy, carbomethoxy, carbopropoxy, acetyl, carbamoyl, carbamoyl substituted with and alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, or halo; (ii) the divalent residue of pyridine, pyrrolidine, imidizole, naphthalene, or thiophene, wherein the divalent bonds are on vicinal ring carbon atoms; (iii) a divalent cycloalkyl of 4-10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl or halo; (iv) di-substituted vinylene, substituted with nitro, cyano, trifluoromethyl, carbethoxy, carbomethoxy, carbopropoxy, acetyl, carbamoyl, carbamoyl substituted with and alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms, or halo; or (v) ethylene, unsubstituted or substituted with 1 to 2 substituents each selected independently from nitro, cyano, trifluoromethyl, carbethoxy, carbomethoxy, carbopropoxy, acetyl, carbamoyl, carbamoyl substituted with and alkyl of 1 to 3 carbon atoms, acetoxy, carboxy, hydroxy, amino, amino, substituted with an alkyl of 1 to 3 carbon atoms, alkyl of 1 to 4 carbon atoms, alkoxy of 1 to 4 carbon atoms, or halo;

$R^6$ is —CO—, —CH$_2$—, —CH$_2$CO—, or —SO$_2$—;

$R^7$ is (i) straight or branched alkyl of 1 to 12 carbon atoms; (ii) cyclic or bicyclic alkyl of to 12 carbon atoms; (iii) pyridyl; (iv) phenyl substituted with one or more substituents each selected independently of the other from nitro, cyano, trifluoromethyl, carbethoxy, carbomethoxy, carbopropoxy; acetyl, carbamoyl, acetoxy, carboxy, hydroxy, amino, straight, branched, cyclic, or bicyclic alkyl of 1 to 10 carbon atoms, straight, branched, cyclic, or bicyclic alkoxy of 1 to 10 carbon atoms, CH$_2$R where R is a cyclic or bicyclic alkyl of 1 to 10 carbon atoms, or halo; (v) benzyl substituted with one to three substituents each selected independently from the group consisting of nitro, cyano, trifluoromethyl, carbethoxy, carbomethoxy, carbopropoxy, acetyl, carbamoyl, acetoxy, carboxy, hydroxy, amino, alkyl of 1 to 4 carbon atoms, alkoxy of 1 to 10 carbon atoms, or halo; (vi) naphthyl; or (vii) benzyloxy; and n has a value of 0, 1, 2, or 3.

Other specific selective cytokine inhibitory drugs include, but are not limited to, the aryl amides (for example, an embodiment being N-benzoyl-3-amino-3-(3',4'-dimethoxyphenyl)-propanamide) of U.S. Pat. Nos. 5,801,195, 5,736,570, 6,046,221 and 6,284,780, each of which is incorporated herein by reference. Representative compounds are of formula:

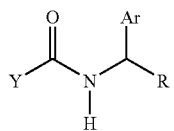

wherein:
Ar is (i) straight, branched, or cyclic, unsubstituted alkyl of 1 to 12 carbon atoms; (ii) straight, branched, or cyclic, substituted alkyl of 1 to 12 carbon atoms; (iii) phenyl; (iv) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, or halo; (v) heterocycle; or (vi) heterocycle substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo;

R is —H, alkyl of 1 to 10 carbon atoms, CH$_2$OH, CH$_2$CH$_2$OH, or CH$_2$COZ where Z is alkoxy of 1 to 10 carbon atoms, benzyloxy, or NHR$^1$ where R$^1$ is H or alkyl of 1 to 10 carbon atoms; and Y is i) a phenyl or heterocyclic ring, unsubstituted or substituted one or more substituents each selected independently one from the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo or ii) naphthyl. Specific examples of the compounds are of formula:

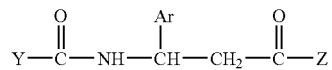

wherein:
Ar is 3,4-disubstituted phenyl where each substituent is selected independently of the other from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo;

Z is alkoxy of 1 to 10 carbon atoms, benzyloxy, amino, or alkylamino of 1 to 10 carbon atoms; and Y is (i) a phenyl, unsubstituted or substituted with one or more substituents each selected, independently one from the other, from the group consisting of nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, and halo, or (ii) naphthyl.

Other specific selective cytokine inhibitory drugs include, but are not limited to, the imide/amide ethers and alcohols (for example, 3-phthalimido-3-(3',4'-dimethoxyphenyl)propan-1-ol) disclosed in U.S. Pat. No. 5,703,098, which is incorporated herein by reference. Representative compounds have the formula:

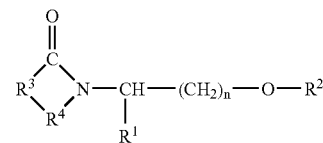

wherein:
R$^1$ is (i) straight, branched, or cyclic, unsubstituted alkyl of 1 to 12 carbon atoms; (ii) straight, branched, or cyclic, substituted alkyl of 1 to 12 carbon atoms; (iii) phenyl; or (iv) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, acylamino, alkylamino, di(alkyl) amino, alkyl of 1 to 10 carbon atoms, cycloalkyl of 3 to 10 carbon atoms, bicycloalkyl of 5 to 12 carbon atoms, alkoxy of 1 to 10 carbon atoms, cycloalkoxy of 3 to 10 carbon atoms, bicycloalkoxy of 5 to 12 carbon atoms, and halo;

R$^2$ is hydrogen, alkyl of 1 to 8 carbon atoms, benzyl pyridylmethyl, or alkoxymethyl;

$R^3$ is (i) ethylene, (ii) vinylene, (iii) a branched alkylene of 3 to 10 carbon atoms, (iv) a branched alkenylene of 3 to 10 carbon atoms, (v) cycloalkylene of 4 to 9 carbon atoms unsubstituted or substituted with one or more substituents each selected independently from the group consisting of nitro, cyano, trifluoromethyl, carbethoxy, carbomethoxy, carbopropoxy, acetyl, carbamoyl, acetoxy, carboxy, hydroxy, amino, amino substituted with alkyl of 1 to 6 carbon atoms, amino substituted with acyl of 1 to 6 carbon atoms, alkyl of 1 to 10 carbon atoms, alkoxy of 1 to 12 carbon atoms, and halo, (vi) cycloalkenylene of 4 to 9 carbon atoms unsubstituted or substituted with one or more substituents each selected independently from the group consisting of nitro, cyano, trifluoromethyl, carbethoxy, carbomethoxy, carbopropoxy, acetyl, carbamoyl, acetoxy, carboxy, hydroxy, amino, amino substituted with alkyl of 1 to 6 carbon atoms, amino substituted with acyl of 1 to 6 carbon atoms, alkyl of 1 to 10 carbon atoms, alkoxy of 1 to 12 carbon atoms, and halo, (vii) o-phenylene unsubstituted or substituted with one or more substituents each selected independently from the group consisting of nitro, cyano, trifluoromethyl, carbethoxy, carbomethoxy, carbopropoxy, acetyl, carbamoyl, acetoxy, carboxy, hydroxy, amino, amino substituted with alkyl of 1 to 6 carbon atoms, amino substituted with acyl of 1 to 6 carbon atoms, alkyl of 1 to 10 carbon atoms, alkoxy of 1 to 12 carbon atoms, and halo, (viii) naphthyl, or (ix) pyridyl;

$R^4$ is —CX—, —CH$_2$— or —CH$_2$CX—;

X is O or S; and n is 0, 1, 2, or 3.

Other specific selective cytokine inhibitory drugs include, but are not limited to, the succinimides and maleimides (for example methyl 3-(3',4',5'6'-petrahydrophthalimdo)-3-(3",4"-dimethoxyphenyl)propionate) disclosed in U.S. Pat. No. 5,658,940, which is incorporated herein by reference. Representative compounds are of formula:

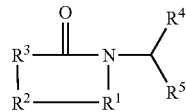

wherein:

$R^1$ is —CH$_2$—, —CH$_2$CO—, or —CO—;

$R^2$ and $R^3$ taken together are (i) ethylene unsubstituted or substituted with alkyl of 1-10 carbon atoms or phenyl, (ii) vinylene substituted with two substituents each selected, independently of the other, from the group consisting of alkyl of 1-10 carbon atoms and phenyl, or (iii) a divalent cycloalkyl of 5-10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl unsubstituted or substituted with alkyl of 1-3 carbon atoms, acetoxy, carboxy, hydroxy, amino, substituted amino, alkyl of 1 to 10 carbon atoms, alkoxy of 1 to 10 carbon atoms, norbornyl, phenyl or halo;

$R^4$ is (i) straight or branched unsubstituted alkyl of 4 to 8 carbon atoms, (ii) cycloalkyl or bicycloalkyl of 5-10 carbon atoms, unsubstituted or substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, branched, straight or cyclic alkyl of 1 to 10 carbon atoms, alkoxy of 1 to 10 carbon atoms, phenyl or halo, (iii) phenyl substituted with one or more substituents each selected independently of the other from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, cycloalkyl or bicyctoalkyl of 3 to 10 carbon atoms, cycloalkoxy or bicycloalkoxy of 3 to 10 carbon atoms, phenyl or halo, (iv) pyridine or pyrrolidine, unsubstituted or substituted with one or more substituents each selected independently of the other from the group consisting of nitro, cyano, trifuoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl or halo; and, $R^5$ is —COX, —CN, —CH$_2$COX, alkyl of 1 to 5 carbon atoms, aryl, —CH$_2$OR, —CH$_2$ aryl, or —CH$_2$OH, where X is NH$_2$, OH, NHR, or OR$^6$, where R is lower alkyl; and where $R^6$ is alkyl or benzyl.

Other specific selective cytokine inhibitory drugs include, but are not limited to, substituted imides (for example, 2-phthalimido-3-(3',4'-dimethoxyphenyl)propane) disclosed in U.S. Pat. No. 6,429,221, which is incorporated herein by reference. Representative compounds have the formula:

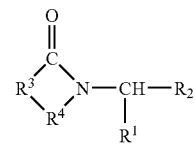

wherein:

$R^1$ is (i) straight, branched, or cyclic alkyl of 1 to 12 carbon atoms, (ii) phenyl or phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, straight or branched alkyl of 1 to 10 carbon atoms, alkoxy of 1 to 10 carbon atoms, or halo, (iii) benzyl or benzyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo, or (iv)-Y-Ph where Y is a straight, branched, or cyclic alkyl of 1 to 12 carbon atoms and Ph is phenyl or phenyl substituted with one or more substituents each selected independently of the other from nitro, cyano, trifluoromethyl, carbethoxy, carbomethoxy, carbopropoxy, acetyl, carbamoyl, acetoxy, carboxy, hydroxy, amino, alkyl of 1 to 10 carbon atoms, alkoxy of 1 to 10 carbon atoms, or halo;

$R^2$ is —H, a branched or unbranched alkyl of 1 to 10 carbon atoms, phenyl, pyridyl, heterocycle, —CH$_2$-aryl, or —CH$_2$-heterocycle;

$R^3$ is i) ethylene, ii) vinylene, iii) a branched alkylene of 3 to 10 carbon atoms, iv) a branched alkenylene of 3 to 10 carbon atoms, v) cycloalkylene of 4 to 9 carbon atoms unsubstituted or substituted with 1 to 2 substituents each selected independently from the group consisting of nitro, cyano, trifluoromethyl, carbethoxy, carbomethoxy, carbopropoxy, acetyl, carbamoyl, acetoxy, carboxy, hydroxy, amino, substituted amino, alkyl of 1 to 4 carbon atoms, alkoxy of 1 to 4 carbon atoms, or halo, vi) cycloalkenylene of 4 to 9 carbon atoms unsubstituted or substituted with 1 to 2 substituents each selected independently from nitro, cyano, trifluoromethyl, carbethoxy, carbomethoxy, carbopropoxy, acetyl, carbamoyl, acetoxy, carboxy, amino, substituted amino, alkyl of 1 to 4 carbon atoms, alkoxy of 1 to 4 carbon atoms, or halo, or vii) o-phenylene unsubstituted or substituted with 1 to 2 substituents each selected independently from nitro, cyano, trifluoromethyl, carbethoxy, carbomethoxy, carbopropoxy, acetyl, carbamoyl, acetoxy, carboxy, hydroxy, amino, substituted amino, alkyl of 1 to 4 carbon atoms, alkoxy 1 to 4 carbon atoms, or halo; and, $R^4$ is —CX, or —$CH_2$—;

X is O or S.

Other specific selective cytokine inhibitory drugs include, but are not limited to, substituted 1,3,4-oxadiazoles (for example, 2-[1-(3-cyclopentyloxy-4-methoxyphenyl)-2-(1,3,4-oxadiazole-2-yl)ethyl]-5-methylisoindoline-1,3-dione) disclosed in U.S. Pat. No. 6,326,388, which is incorporated herein by reference. Representative compounds are of formula:

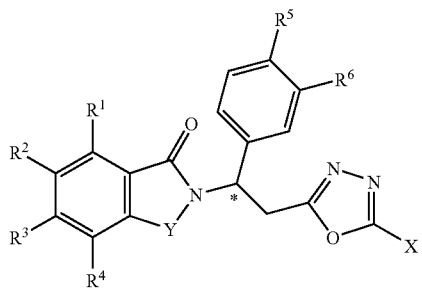

wherein:

the carbon atom designated* constitutes a center of chirality,

Y is C=O, $CH_2$, $SO_2$ or $CH_2C$=O;

X is hydrogen, or alkyl of 1 to 4 carbon atoms;

each of $R^1$, $R^2$, $R^3$, and $R^4$, independently of the others, is hydrogen, halo, trifluoromethyl, acetyl, alkyl of 1 to 8 carbon atoms, alkoxy of 1 to 4 carbon atoms, nitro, cyano, hydroxy, —$CH_2NR^8R^9$, —$(CH_2)_2NR^8R^9$, or —$NR^8R^9$ or any two of $R^1$, $R^2$, $R^3$, and $R^4$ on adjacent carbon atoms, together with the depicted benzene ring are naphthylidene, quinoline, quinoxaline, benzimidazole, benzodioxole or 2-hydroxybenzimidazole;

each of $R^5$ and $R^6$, independently of the other, is hydrogen, alkyl of 1 to 4 carbon atoms, alkoxy of 1 to 6 carbon atoms, cyano, benzocycloalkoxy, cycloalkoxy of up to 18 carbon atoms, bicyloalkoxy of up to 18 carbon atoms, tricylcoalkoxy of up to 18 carbon atoms, or cycloalkylalkoxy of up to 18 carbon atoms;

each of $R^8$ and $R^9$, taken independently of the other is hydrogen, straight or branched alkyl of 1 to 8 carbon atoms, phenyl, benzyl, pyridyl, pyridylmethyl, or one of $R^8$ and $R^9$ is hydrogen and the other is —$COR^{10}$, or —$SO_2R^{10}$, or $R^8$ and $R^9$ taken together are tetramethylene, pentamethylene, hexamethylene, —CH=NCH=CH—, or —$CH_2CH_2X^1CH_2CH_2$— in which $X^1$ is —O—, —S—, or —NH—

$R^{10}$ is hydrogen, alkyl of 1 to 8 carbon atoms, cycloalkyl, cycloalkylmethyl of up to 6 carbon atoms, phenyl, pyridyl, benzyl, imidazolylmethyl, pyridylmethyl, $NR^{11}R^{12}$, $CH_2R^{14}R^{15}$, or $NR^{11}R^{12}$ wherein $R^{14}$ and $R^{15}$, independently of each other, are hydrogen, methyl, ethyl, or propyl, and wherein $R^{11}$ and $R^{12}$, independently of each other, are hydrogen, alkyl of 1 to 8 carbon atoms, phenyl, or benzyl; and the acid addition salts of said compounds which contain a nitrogen atom susceptible of protonation.

Specific examples of the compounds are of formula:

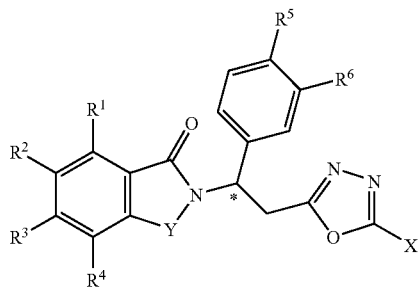

wherein:

the carbon atom designated* constitutes a center of chirality,

Y is C=O, $CH_2$, $SO_2$ or $CH_2C$=O;

X is hydrogen, or alkyl of 1 to 4 carbon atoms;

(i) each of $R^1$, $R^2$, $R^3$, and $R^4$, independently of the others, is hydrogen, halo, trifluoromethyl, acetyl, alkyl of 1 to 8 carbon atoms, alkoxy of 1 to 4 carbon atoms, nitro, cyano, hydroxy, —$CH_2NR^8R^9$, —$(CH_2)_2NR^8R^9$, or —$NR^8R^9$ or (ii) any two of $R^1$, $R^2$, $R^3$, and $R^4$ on adjacent carbon atoms, together with the depicted benzene ring to which they are bound are naphthylidene, quinoline, quinoxaline, benzimidazole, benzodioxole or 2-hydroxybenzimidazole;

each of $R^5$ and $R^6$, independently of the other, is hydrogen, alkyl of 1 to 4 carbon atoms, alkoxy of 1 to 6 carbon atoms, cyano, benzocycloalkoxy, cycloalkoxy of up to 18 carbon atoms, bicyloalkoxy of up to 18 carbon atoms, tricylcoalkoxy of up to 18 carbon atoms, or cycloalkylalkoxy of up to 18 carbon atoms;

(i) each of $R^8$ and $R^9$, independently of the other, is hydrogen, alkyl of 1 to 8 carbon atoms, phenyl, benzyl, pyridyl, pyridylmethyl, or (ii) one of $R^8$ and $R^9$ is hydrogen and the other is —$COR^{10}$, or —$SO_2R^{10}$, in which $R^{10}$ is hydrogen, alkyl of 1 to 8 carbon atoms, cycloalkyl, cycloalkylmethyl of up to 6 carbon atoms, phenyl, pyridyl, benzyl, imidazolylmethyl, pyridylmethyl, $NR^{11}R^{12}$, or $CH_2NR^{14}R^{15}$, wherein $R^{11}$ and $R^{12}$, independently of each other, are hydrogen, alkyl of 1 to 8 carbon atoms, phenyl, or benzyl and $R^{14}$ and $R^{15}$, independently of each other, are hydrogen, methyl, ethyl, or propyl; or (iii) $R^8$ and $R^9$ taken together are tetramethylene, pentamethylene, hexamethylene, —CH=NCH=CH—, or —$CH_2CH_2X^1CH_2CH_2$— in which $X^1$ is —O—, —S—, or —NH—.

Other specific selective cytokine inhibitory drugs include, but are not limited to, cyano and carboxy derivatives of substituted styrenes (for example, 3,3-bis-(3,4-dimethoxyphenyl)acrylonitrile) disclosed in U.S. Pat. Nos. 5,929,117, 6,130,226, 6,262,101 and 6,479,554, each of which is incorporated herein by reference. Representative compounds are of formula:

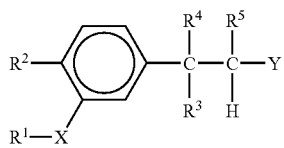

wherein:

(a) X is —O— or —(C$_n$H$_{2n}$)— in which n has a value of 0, 1, 2, or 3, and R$^1$ is alkyl of one to 10 carbon atoms, monocycloalkyl of up to 10 carbon atoms, polycycloalkyl of up to 10 carbon atoms, or benzocyclic alkyl of up to 10 carbon atoms or (b) X is —CH= and R$^1$ is alkylidene of up to 10 carbon atoms, monocycloalkylidene of up to 10 carbon atoms, or bicycloalkylidene of up to 10 carbon atoms;

R$^2$ is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkylidenemethyl, lower alkoxy, or halo;

R$^3$ is (i) phenyl, unsubstituted or substituted with 1 or more substituents each selected independently from nitro, cyano, halo, trifluoromethyl, carbethoxy, carbomethoxy, carbopropoxy, acetyl, carbamoyl, carbamoyl substituted with alkyl of 1 to 3 carbon atoms, acetoxy, carboxy, hydroxy, amino, amino substituted with an alkyl of 1 to 5 carbon atoms, alkyl of up to 10 carbon atoms, cycloalkyl of up to 10 carbon atoms, alkoxy of up to 10 carbon atoms, cycloalkoxy of up to 10 carbon atoms, alkylidenemethyl of up to 10 carbon atoms, cycloalkylidenemethyl of up to 10 carbon atoms, phenyl, or methylenedioxy; (ii) pyridine, substituted pyridine, pyrrolidine, imidizole, naphthalene, or thiophene; (iii) cycloalkyl of 4-10 carbon atoms, unsubstituted or substituted with 1 or more substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl;

each of R$^4$ and R$^5$ taken individually is hydrogen or R$^4$ and R$^5$ taken together are a carbon-carbon bond;

Y is —COZ, —C≡N, or lower alkyl of 1 to 5 carbon atoms;

Z is —OH, —NR$^6$R$^6$, —R$^7$, or —OR$^7$; R$^6$ is hydrogen or lower alkyl; and R$^7$ alkyl or enzyl. Specific examples of the compounds are of formula:

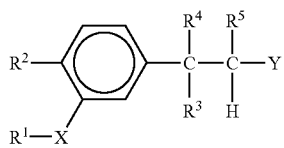

wherein:

(a) X is —O— or —(C$_n$H$_{2n}$)— in which n has a value of 0, 1, 2, or 3, and R$^1$ is alkyl of one to 10 carbon atoms, monocycloalkyl of up to 10 carbon atoms, polycycloalkyl of up to 10 carbon atoms, or benzocyclic alkyl of up to 10 carbon atoms, or (b) X is —CH= and R$^1$ is alkylidene of up to 10 carbon atoms, monocycloalkylidene of up to 10 carbon atoms, or bicycloalkylidene of up to 10 carbon atoms;

R$^2$ is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkylidenemethyl, lower alkoxy, or halo;

R$^3$ is pyrrolidine, imidazole or thiophene unsubstituted or substituted with 1 or more substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, or phenyl;

each of R$^4$ and R$^5$ taken individually is hydrogen or R$^4$ and R$^5$ taken together are a carbon-carbon bond;

Y is —COZ, —C≡N, or lower alkyl of 1 to 5 carbon atoms;

Z is —OH, —NR$^6$R$^6$, —R$^7$, or —OR$^7$; R$^6$ is hydrogen or lower alkyl; and R$^7$ alkyl or benzyl.

Particularly preferred nitriles are compounds of the formula:

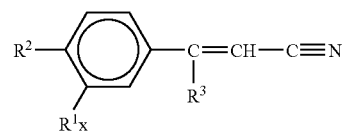

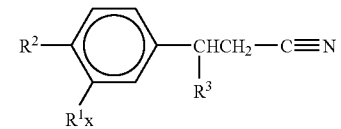

wherein:

(a) X is —O— or —(C$_n$H$_{2n}$)— in which n has a value of 0, 1, 2, or 3, and R$^1$ is alkyl of up to 10 carbon atoms, monocycloalkyl of up to 10 carbon atoms, polycycloalkyl of up to 10 carbon atoms, or benzocyclic alkyl of up to 10 carbon atoms, or (b) X is —CH=, and R$^1$ is alkylidene of up to 10 carbon atoms or monocycloalkylidene of up to 10 carbon atoms;

R$^2$ is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkoxy, or halo; and R$^3$ is (i) phenyl or naphthyl, unsubstituted or substituted with 1 or more substituents each selected independently from nitro, cyano, halo, trifluoromethyl, carbethoxy, carbomethoxy, carbopropoxy, acetyl, carbamoyl, or carbamoyl substituted with alkyl of 1 to 3 carbon atoms, acetoxy, carboxy, hydroxy, amino, amino substituted with an alkyl of 1 to 5 carbon atoms, alkoxy or cycloalkoxy of 1 to 10 carbon atoms; or (ii) cycloalkyl of 4 to 10 carbon atoms, unsubstituted or substituted with one or more substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, or phenyl.

Particularly preferred nitrile is of formula:

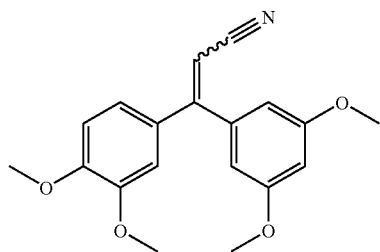

Other specific selective cytokine inhibitory drugs include, but are not limited to, isoindoline-1-one and isoindoline-1,3-dione substituted in the 2-position with an α-(3,4-disubstituted phenyl)alkyl group and in the 4- and/or 5-position with a nitrogen-containing group disclosed in WO 01/34606, which is incorporated herein by reference. Representative compounds are of formula:

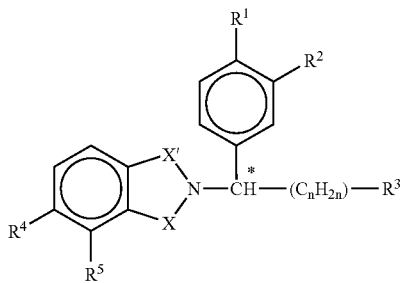

wherein:

the carbon atom designated constitutes a center of chirality;

each of $R^1$ and $R^2$, independently of the other, is alkyl of 1 to 4 carbon atoms, alkoxy of 1 to 4 carbon atoms, cyano, cycloalkoxy of 3 to 18 carbon atoms, cycloalkyl of 3 to 18 carbon atoms, or cycloalkylmethoxy in which cycloalkyl has from 3 to 18 carbon atoms;

one of X and X' is =C=O or =SO$_2$ and the other of X and X' is a divalent group selected from =C=O, =CH$_2$, =SO$_2$ or =CH$_2$C=O;

n has a value of 1, 2, or 3;

$R^3$ is —SO$_2$—Y, —COZ, —CN, or hydroxyalkyl of 1 to 6 carbon atoms in which

Y is alkyl of 1 to 6 carbon atoms, phenyl, or benzyl;

Z is —NR$^{6''}$R$^{7''}$, alkyl of 1 to 6 carbon atoms, phenyl, or benzyl;

$R^{6''}$ is hydrogen, alkyl of 1 to 4 carbon atoms, cycloalkyl of 3 to 18 carbon atoms; phenyl, benzyl, or alkanoyl of 2 to 5 carbon atoms, each of which is unsubstituted or substituted with halo, amino, or alkylamino of 1 to 4 carbon atoms; and $R^{7''}$ is hydrogen or alkyl of 1 to 4 carbon atoms;

$R^4$ and $R^5$ (i) when taken together, are —NH—CH$_2$—R$^8$—, —NH—CO—R$^8$— or —N=CH—R$^8$— in which —R$^8$— is —CH$_2$—, —O—, —NH—, —CH=CH—, —CH=N—, or —N=CH—, or, (ii) when taken independently of each other, one of $R^4$ and $R^5$ is hydrogen and the other of $R^4$ and $R^5$ is imidazolyl, pyrrolyl; oxadiazolyl, triazolyl, or

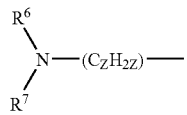

in which z is 0 or 1;

$R^6$, when taken independently of $R^7$, is hydrogen; alkyl of 1 to 4 carbon atoms, cycloalkyl of 3 to 18 carbon atoms, alkanoyl of 2 to 5 carbon atoms, or cycloalkanoyl of 2 to 6 carbon atoms, each of which is unsubstituted or substituted with halo, amino, monoalkylamino or dialkylamino in which each alkyl group contains 1 to 4 carbon atoms; phenyl; benzyl; benzoyl; alkoxycarbonyl of 2 to 5 carbon atoms; alkoxyalkylcarbonyl of 2 to 5 carbon atoms; N-morpholinocarbonyl; carbamoyl; N-substituted carbamoyl in which the substituent is alkyl of 1 to 4 carbon atoms, cycloalkyl of 3 to 18 carbon atoms, or alkanoyl of 2 to 5 carbon atoms, each of which is unsubstituted or substituted with halo, amino, monoalkylamino or dialkylamino in which each alkyl group contains 1 to 4 carbon atoms; phenyl; benzyl; or methylsulfonyl; and $R^7$ is hydrogen, alkyl of 1 to 4 carbon atoms, methylsufonyl; or alkoxyalkylcarbonyl of 2 to 5 carbon atoms. Preferably, z is not 0 when (i) $R^3$ is —SO$_2$—Y, —COZ, or —CN and (ii) $R^4$ or $R^5$ is hydrogen. When taken together, $R^6$ and $R^7$ can be —CH=CH—CH=CH—, —CH=CH—N=CH—, or alkylidene of 1 or 2 carbon atomes substituted by amino, alkylamino, or dialkylamino in which each alkyl group has from 1 to 4 carbon atoms. In addition, one of $R^4$ and $R^5$ is

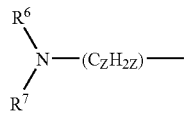

in which each of $R^6$, $R^7$, and z is as defined above; and the other of $R^4$ and $R^5$ is

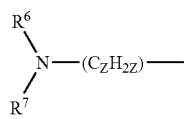

in which z' is 0 or 1;

$R^{6'}$ has the same meaning as, but is selected independently of, $R^6$;

$R^{7'}$ has the same meaning as, but is selected independently of, $R^7$.

Specific examples of the compounds are of formula:

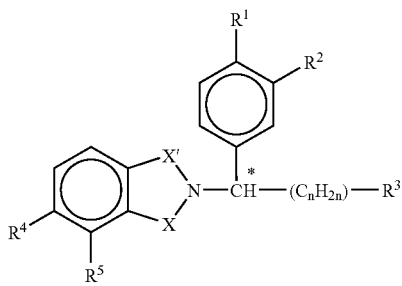

wherein:

each of $R^1$ and $R^2$, independently of the other, is alkyl of 1 to 4 carbon atoms, alkoxy of 1 to 4 carbon atoms, cyano, cycloalkoxy of 3 to 18 carbon atoms, cycloalkyl of 3 to 18 carbon atoms, or cycloalkylmethoxy in which cycloalkyl has from 3 to 18 carbon atoms;

one of X and X' is =C=O or =SO$_2$ and the other of X and X' is a divalent group selected from =C=O, =CH$_2$, =SO$_2$ or CH$_2$CO;

$R^3$ is —SO$_2$—Y, —COZ, —CN, or hydroxyalkyl of 1 to 6 carbon atoms in which

Y is alkyl of 1 to 6 carbon atoms, phenyl, or benzyl;

Z is —NR$^{6''}$, R$^{7''}$, alkyl of 1 to 6 carbon atoms, phenyl, or benzyl;

$R^{6''}$ is hydrogen, alkyl of 1 to 4 carbon atoms, cycloalkyl of 3 to 18 carbon atoms; phenyl, benzyl, or alkanoyl of 2 to 5 carbon atoms, each of which is unsubstituted or substituted with halo, amino, or alkylamino of 1 to 4 carbon atoms;

$R^{7''}$ is hydrogen or alkyl of 1 to 4 carbon atoms;

n has a value of 1, 2, or 3;

(i) $R^4$ and $R^5$ when taken together, are —NH—CH$_2$—R$^8$—, —NH—CO—R$^8$— or —N=CH—$^8$— in which —R$^8$— is —CH$_2$—, —O—, —NH—, —CH=CH—, —CH=N—, or —N=CH—, or, (ii) when taken independently of each other, (1) one of $R^4$ and $R^5$ is hydrogen and the other of $R^4$ and $R^5$ is imidazolyl, pyrrolyl; oxadiazolyl, triazolyl, or

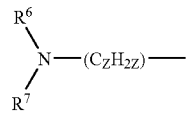

in which z is 0 or 1 provided z is not 0 when (i) $R^3$ is —SO$_2$—Y, —COZ, or —CN and (ii) $R^4$ or $R^5$ is hydrogen;

$R^6$, when taken independently of $R^7$, is hydrogen; alkyl of 1 to 4 carbon atoms, cycloalkyl of 3 to 18 carbon atoms, alkanoyl of 2 to 5 carbon atoms, or cycloalkanoyl of 2 to 6 carbon atoms each of which is unsubstituted or substituted with halo, amino, monoalkylamino or dialkylamino in which each alkyl group contains 1 to 4 carbon atoms; phenyl; benzyl; benzoyl; alkoxycarbonyl of 2 to 5 carbon atoms; alkoxyalkylcarbonyl of 2 to 5 carbon atoms; N-morpholinocarbonyl; carbamoyl; N-substituted carbamoyl in which the substituent is alkyl of 1 to 4 carbon atoms, cycloalkyl of 3 to 18 carbon atoms, or, alkanoyl of 2 to 5 carbon atoms, each of which is unsubstituted or substituted with halo, amino, monoalkylamino or dialkylamino in which each alkyl group contains 1 to 4 carbon atoms; phenyl; benzyl; or methylsulfonyl; and $R^7$ is hydrogen, alkyl of 1 to 4 carbon atoms, methylsulfonyl; or alkoxyalkylcarbonyl of 2 to 5 carbon atoms;

$R^6$ and $R^7$ taken together are —CH=CH—CH=CH—, —CH=CH—N=CH—, or alkylidene of 1 or 2 carbon atoms substituted by amino, alkylamino, or dialkylamino in which each alkyl group has from 1 to 4 carbon atoms; or (2) one of $R^4$ and $R^5$ is

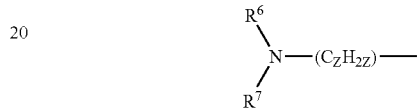

in which each of $R^6$, $R^7$, and z is as defined above; and the other of $R^4$ and $R^5$ is

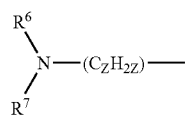

in which z' is 0 or 1;

$R^{6'}$ has the same meaning as, but is selected independently of, $R^6$;

$R^{7'}$ has the same meaning as, but is selected independently of, $R^7$; and the carbon atom designated constitutes a center of chirality. Specific compounds are of formula:

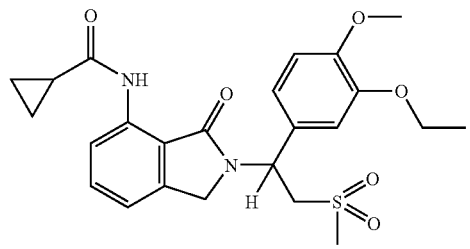

and the enantiomers thereof. Still other specific selective cytokine inhibitory drugs include, but are not limited to, imido and amido substituted acylhydroxamic acids (for example, (3-(1,3-dioxoisoindoline-2-yl)-3-(3-ethoxy-4-methoxyphenyl)propanoylamino) propanoate disclosed in WO 01/45702, which is incorporated herein by reference. Representative compounds are of formula:

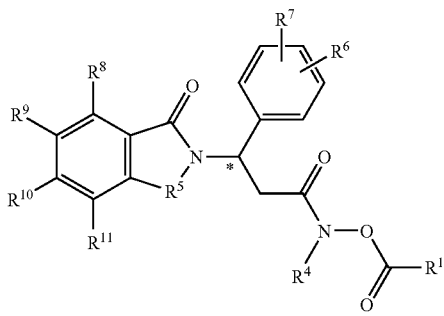

wherein:
the carbon atom designated constitutes a center of chirality, $R^4$ is hydrogen or —(C=O)—$R^{12}$ each of $R^1$ and $R^{12}$, independently of each other, is alkyl of 1 to 6 carbon atoms, phenyl, benzyl, pyridyl methyl, pyridyl, imidazoyl, imidazolyl methyl, or CHR*(CH$_2$)$_n$NR*R° wherein R* and R°, independently of the other, are hydrogen, alkyl of 1 to 6 carbon atoms, phenyl, benzyl, pyridyl methyl, pyridyl, imidazoyl or imidazolylmethlyl, and n=0, 1, or 2;

$R^5$ is C=O, CH$_2$, CH$_2$—CO—, or SO$_2$;

each of $R^6$ and $R^7$, independently of the other, is nitro, cyano, trifluoromethyl, carbethoxy, carbomethoxy, carbopropoxy, acetyl, carbamoyl, acetoxy, carboxy, hydroxy, amino, alkyl of 1 to 6 carbon atoms, alkoxy of 1 to 6 carbon atoms, cycloalkoxy of 3 to 8 carbon atoms, halo, bicycloalkyl of up to 18 carbon atoms, tricycloalkoxy of up to 18 carbon atoms, 1-indanyloxy, 2-indanyloxy, C$_4$-C$_8$-cycloalkylidenemethyl, or C$_3$-C$_{10}$-alkylidenemethyl;

each of $R^8$, $R^9$, $R^{10}$, and $R^{11}$, independently of the others, is (i) hydrogen, nitro, cyano, trifluoromethyl, carbethoxy, carbomethoxy, carbopropoxy, acetyl, carbamoyl, acetoxy, carboxy, hydroxy, amino, alkylamino, dialkylamino, acylamino, alkyl of 1 to 10 carbon atoms, alkoxy of 1 to 10 carbon atoms, halo, or (ii) one of $R^8$, $R^9$, $R^{10}$, and $R^{11}$ is acylamino comprising a lower alkyl, and the remaining of $R^8$, $R^9$, $R^{10}$, and $R^{11}$ are hydrogen, or (iii) hydrogen if $R^8$ and $R^9$ taken together are benzo, quinoline, quinoxaline, benzimidazole, benzodioxole, 2-hydroxybenzimidazole, methylenedioxy, dialkoxy, or dialkyl, or (iv) hydrogen if $R^{10}$ and $R^{11}$, taken together are benzo, quinoline, quinoxaline, benzimidazole, benzodioxole, 2-hydroxybenzimidazole, methylenedioxy, dialkoxy, or dialkyl, or (v) hydrogen if $R^9$ and $R^{10}$ taken together are benzo.

Compounds of the invention can either be commercially purchased or prepared according to the methods described in the patents or patent publications disclosed herein. Further, optically pure compositions can be asymmetrically synthesized or resolved using known resolving agents or chiral columns as well as other standard synthetic organic chemistry techniques.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases known in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine N-methylglucamine), lysine, and procaine.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of selective cytokine inhibitory drugs that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of a selective cytokine inhibitory drug that comprise —NO, —NO$_2$, —ONO, or —ONO$_2$ moieties. Prodrugs can typically be prepared using well-known methods, such as those described in 1*Burger's Medicinal Chemistry and Drug Discovery*, 172-178, 949-982 (Manfred E. Wolff ed., 5th ed. 1995), and *Design of Prodrugs* (H. Bundgaard ed., Elselvier, N.Y. 1985).

As used herein and unless otherwise indicated, the terms "biohydrolyzable amide," "biohydrolyzable ester," "biohydrolyzable carbamate," "biohydrolyzable carbonate," "biohydrolyzable ureide," and "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

Various selective cytokine inhibitory drugs contain one or more chiral centers, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of selective cytokine inhibitory drugs may be used in methods and compositions of the invention. The purified (R) or (S) enantiomers of the specific compounds disclosed herein may be used substantially free of its other enantiomer.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound.

As used herein and unless otherwise indicated, the term "enantiomerically pure" means a stereomerically pure composition of a compound having one chiral center. Similarly, the term "enantiomerically enriched" means a stereomerically enriched composition of a compound having one chiral center.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4.2. Second Active Agents

Selective cytokine inhibitory drugs can be combined with other pharmacologically active compounds ("second active agents") in methods and compositions of the invention. It is believed that certain combinations work synergistically in the treatment of particular types of cancer and certain diseases and conditions associated with, or characterized by, undesired angiogenesis. Selective cytokine inhibitory drugs can also work to alleviate adverse effects associated with certain second active agents, and some second active agents can be used to alleviate adverse effects associated with selective cytokine inhibitory drugs.

One or more second active ingredients or agents can be used in the methods and compositions of the invention together with a selective cytokine inhibitory drug. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Typical large molecule active agents are biological molecules, such as naturally occurring or artificially made proteins. Proteins that are particularly useful in this invention include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions of the invention include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393, 870; and 5,229,496; all of which are incorporated herein by reference. Recombinant and mutated forms of G-CSF can be prepared as described in U.S. Pat. Nos. 4,810,643; 4,999, 291; 5,528,823; and 5,580,755; all of which are incorporated herein by reference.

This invention encompasses the use of native, naturally occurring, and recombinant proteins. The invention further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with compounds of the invention include monoclonal and polyclonal antibodies. Examples of antibodies include, but are not limited to, trastuzumab (Herceptin®), rituximab (Rituxan®),bevacizumab (Avastin™), pertuzumab (Omnitarg™), tositumomab (Bexxar®), edrecolomab (Panorex®), and G250. Compounds of the invention can also be combined with, or used in combination with, anti-TNF-α antibodies.

Large molecule active agents may be administered in the form of anti-cancer vaccines. For example, vaccines that secrete, or cause the secretion of, cytokines such as IL-2; G-CSF, and GM-CSF can be used in the methods, pharmaceutical compositions, and kits of the invention. See, e.g., Emens, L. A., et al., *Curr. Opinion Mol. Ther.* 3(1):77-84 (2001).

In one embodiment of the invention, the large molecule active agent reduces, eliminates, or prevents an adverse effect associated with the administration of a selective cytokine inhibitory drug. Depending on the particular selective cytokine inhibitory drug and the disease or disorder begin treated, adverse effects can include, but are not limited to, drowsiness and somnolence, dizziness and orthostatic hypotension, neutropenia, infections that result from neutropenia, increased HIV-viral load, bradycardia, Stevens-Johnson Syndrome and toxic epidermal necrolysis, and seizures (e.g., grand mal convulsions). A specific adverse effect is neutropenia.

Second active agents that are small molecules can also be used to alleviate adverse effects associated with the administration of a selective cytokine inhibitory drug. However, like some large molecules, many are believed to be capable of providing a synergistic effect when administered with (e.g., before, after or simultaneously) a selective cytokine inhibitory drug. Examples of small molecule second active agents include, but are not limited to, anti-cancer agents, antibiotics, immunosuppressive agents, and steroids.

Examples of anti-cancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acyflilvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximie; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ihnofosine; ilomastat; imatinib (e.g., Gleevec®), imiquimod; immunostirnulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole;

liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; milimostim; mitoguazone; mitolactol; mitomycin analogues; mitonafide; mitotoxin fibroblast growth factor-saporin; mitoxantrone; mofarotene; molgramostim;Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, oblimersen (Genasense®) remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

4.3. Methods of Treatments and Prevention

Methods of this invention encompass methods of treating, preventing and/or managing various types of cancer and diseases and disorders associated with, or characterized by, undesired angiogenesis. As used herein, unless otherwise specified, the term "treating" refers to the administration of a compound of the invention or other additional active agent after the onset of symptoms of the particular disease or disorder. As used herein, unless otherwise specified, the term "preventing" refers to the administration prior to the onset of symptoms, particularly to patients at risk of cancer, and other diseases and disorders associated with, or characterized by, undesired angiogenesis. The term "prevention" includes the inhibition of a symptom of the particular disease or disorder. Patients with familial history of cancer and diseases and disorders associated with, or characterized by, undesired angiogenesis are preferred candidates for preventive regimens. As used herein and unless otherwise indicated, the term "managing" encompasses preventing the recurrence of the particular disease or disorder in a patient who had suffered from it, and/or lengthening the time a patient who had suffered from the disease or disorder remains in remission.

As used herein, the term "cancer" includes, but is not limited to, solid tumors and blood born tumors. The term "cancer" refers to disease of skin tissues, organs, blood, and vessels, including, but not limited to, cancers of the bladder, bone or blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, sceloderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistance to chemotherapy or radiation; in particular, refractory to thalidomide.

As used herein to refer to diseases and conditions other than cancer, the terms "diseases or disorders associated with, or characterized by, undesired angiogenesis," "diseases or disorders associated with undesired angiogenesis," and "diseases or disorders characterized by undesired angiogenesis" refer to diseases, disorders and conditions that are caused, mediated or attended by undesired, unwanted or uncontrolled angiogenesis, including, but not limited to, inflammatory diseases, autoimmune diseases, genetic diseases, allergic diseases, bacterial diseases, ocular neovascular diseases, choroidal neovascular diseases, and retina neovascular diseases.

Examples of such diseases or disorders associated with undesired angiogenesis include, but are not limited to, diabetic retinopathy, retinopathy of prematurity, corneal graft rejection, neovascular glaucoma, retrolental fibroplasia, proliferative vitreoretinopathy, trachoma, myopia, optic pits, epidemic keratoconjunctivitis, atopic keratitis, superior limbic keratitis, pterygium keratitis sicca, sjogrens, acne rosacea, phylectenulosis, syphilis, lipid degeneration, bacterial ulcer, fungal ulcer, Herpes simplex infection, Herpes zoster infection, protozoan infection, Kaposi sarcoma, Mooren ulcer, Terrien's marginal degeneration, mariginal keratolysis, rheumatoid arthritis, systemic lupus, polyarteritis, trauma, Wegeners sarcoidosis, scleritis, Steven's Johnson disease, periphigoid radial keratotomy, sickle cell anemia, sarcoid, pseudoxanthoma elasticum, Pagets disease, vein occlusion, artery occlusion, carotid obstructive disease, chronic uveitis, chronic vitritis, Lyme's disease, Eales disease, Bechet's disease, retinitis, choroiditis, presumed ocular histoplasmosis, Bests disease, Stargarts disease, pars planitis, chronic retinal detachment, hyperviscosity syndromes, toxoplasmosis, rubeosis, sarcodisis, sclerosis, soriatis, psoriasis, primary sclerosing cholangitis, proctitis, primary biliary srosis, idiopathic pulmonary fibrosis, alcoholic hepatitis, endotoxemia, toxic shock syndrome, osteoarthritis, retrovirus replication, wasting, meningitis, silica-induced fibrosis, asbestos-induced fibrosis, malignancy-associated hypercalcemia, stroke, circulatory shock, periodontitis, gingivitis, macrocytic anemia, refractory anemia, 5q-syndrome, and veterinary disorder caused by feline immunodeficiency virus, equine infectious anemia virus, caprine arthritis virus, visna virus, maedi virus or lenti virus.

In specific embodiments of the invention, diseases or disorders associated with undesired angiogenesis do not include congestive heart failure, cardiomyopathy, pulmonary edema, endotoxin-mediated septic shock, acute viral myocarditis, cardiac allograft rejection, myocardial infarction, HIV, hepatitis, adult respiratory distress syndrome, bone-resorption disease, chronic obstructive pulmonary diseases, chronic pulmonary inflammatory disease, dermatitis, cystic fibrosis, septic shock, sepsis, endotoxic shock, hemodynamic shock, sepsis syndrome, post ischemic reperfusion injury, fibrotic disease, cachexia, graft rejection, rheumatoid spondylitis, osteoporosis, ulcerative colitis, inflammatory-bowel disease, multiple sclerosis, systemic lupus erythrematosus, erythema nodosum leprosum in leprosy, radiation damage, asthma, hyperoxic alveolar injury, malaria, mycobacterial infection, and opportunistic infections resulting from HIV.

This invention encompasses methods of treating patients who have been previously treated for cancer or diseases or disorders associated with, or characterized by, undesired angiogenesis, but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not. Because patients with cancer and diseases and disorders characterized by undesired angiogenesis have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer and other diseases or disorders.

Methods encompassed by this invention comprise administering one or more selective cytokine inhibitory drug of the invention, or a pharmaceutically acceptable salt, solvate, hydrate, stereoisomer, clathrate, or prodrug thereof, to a patient (e.g., a human) suffering, or likely to suffer, from cancer or a disease or disorder mediated by undesired angiogenesis.

In one embodiment of the invention, the recommended daily dose range of a selective cytokine inhibitory drug for the conditions described herein lie within the range of from about 1 mg to about 10,000 mg per day, given as a single once-a-day dose, or preferably in divided doses throughout a day. More specifically, the daily dose is administered twice daily in equally divided doses. Specifically, a daily dose range should be from about 1 mg to about 5,000 mg per day, more specifically, between about 10 mg and about 2,500 mg per day, between about 100 mg and about 800 mg per day, between about 100 mg and about 1,200 mg per day, or between about 25 mg and about 2,500 mg per day. In managing the patient, the therapy should be initiated at a lower dose, perhaps about 1 mg to about 2,500 mg, and increased if necessary up to about 200 mg to about 5,000 mg per day as either a single dose or divided doses, depending on the patient's global response. In a particular embodiment, 3-(3,4-dimethoxy-phenyl)-3-(1-oxo-1,3-dihydro-isoindol-2-yl)-propionamide can be preferably administered in an amount of about 400, 800, 1,200, 2,500, 5,000 or 10,000 mg a day as two divided doses.

In a specific embodiment, 3-(3,4-dimethoxy-phenyl)-3-(1-oxo-1,3-dihydro-isoindol-2-yl)-propionamide may be administered in an amount of about 400, 800, or 1,200 mg per day to patients with relapsed multiple myeloma. In a particular embodiment, 3-(3,4-dimethoxy-phenyl)-3-(1-oxo-1,3-dihydro-isoindol-2-yl)-propionamide may be administered initially in an amount of 100 mg/day and the dose can be escalated every week to 200, 400, 800, 1,200, and 2,500 mg/day. In a specific embodiment, the compound can be administered in an amount of up to about 5,000 mg/day to patients with solid tumor. In a particular embodiment, the compound can be administered in an amount of up to about 10,000 mg/day to patients with glioma.

In a specific embodiment, 3-(3,4-dimethoxy-phenyl)-3-(1-oxo-1,3-dihydro-isoindol-2-yl)-propionamide may be administered to patients with Crohn's disease initially in an amount of 400 mg and can be escalated to 800 mg and 1200 mg daily.

In a specific embodiment, 3-(3,4-dimethoxy-phenyl)-3-(1-oxo-1,3-dihydro-isoindol-2-yl)-propionamide may be administered in an amount of from about 100 mg to about 5,000 mg per day or about 1.5 to 2.5 times the daily dose every other day, to patients with diseases or disorders associated with, or characterized by, undesired angiogenesis including, but not limited to, endotoxemia, toxic shock syndrome, osteoarthritis, retrovirus replication, wasting, meningitis, silica-induced fibrosis, asbestos-induced fibrosis, veterinary disorder, malignancy-associated hypercalcemia, stroke, circulatory shock, periodontitis, gingivitis, macrocytic anemia, refractory anemia, and 5q-syndrome.

In another-specific embodiment, (+)-2-[1-(3-ethoxy-4-methoxyphenyl)-2-methylsulfonylethyl]-4 acetylaminoisoindoline 1,3-dione is administered in an amount of about 1 to about 200 mg/day, preferably about 10 to about 50 mg/day, or a greater dose, generally about 1.5 to 2.5 times the daily dose every other day, to patients with diseases or disorders associated with, or characterized by, undesired angiogenesis including, but not limited to, endotoxemia, toxic shock syndrome, osteoarthritis, retrovirus replication, wasting, meningitis, silica-induced fibrosis, asbestos-induced fibrosis, veterinary disorder, malignancy-associated hypercalcemia, stroke, circulatory shock, periodontitis, gingivitis, macrocytic anemia, refractory anemia, and 5q-syndrome.

4.3.1. Combination Therapy with a Second Active Agent

Specific methods of the invention comprise administering a selective cytokine inhibitory drug of the invention, or a pharmaceutically acceptable salt, solvate, hydrate, stereoisomer, clathrate, or prodrug thereof, in combination with one or more second active agents, and/or in combination with radiation therapy, blood transfusions, or surgery. Examples of selective cytokine inhibitory drugs of the invention are disclosed herein (see, e.g., section 4.1). Examples of second active agents are also disclosed herein (see, e.g., section 4.2).

Administration of the selective cytokine inhibitory drugs and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease eing treated. A preferred route of administration for a selective cytokine inhibitory drug of the invention is oral or ophthalmic. Preferred routes of administration for the second active gents or ingredients of the invention are known to those of ordinary skill in the art. See, e.g., *Physicians' Desk Reference,* 1755-1760 (56$^{th}$ ed., 2002).

In one embodiment of the invention, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount (s) of selective cytokine inhibitory drugs of the invention and any optional additional active agents concurrently administered to the patient. In a particular embodiment, the second active agent is oblimersen (Genasense®), GM-CSF, G-CSF, EPO, taxotere, irinotecan, dacarbazine, transretinoic acid, topotecan, pentoxifylline, ciprofloxacin, dexamethasone, vincristine, doxorubicin, cox-2 inhibitors, IL2, IL8, IL18, IFN, Ara-C, vinorelbine, or a combination thereof.

In a particular embodiment, GM-CSF, G-CSF or EPO is administered subcutaneously during about five days in a four or six week cycle in an amount of from about 1 to about 750 mg/m$^2$/day, preferably in an amount of from about 25 to about 500 mg/m$^2$/day, more preferably in an amount of from about 50 to about 250 mg/m$^2$/day, and most preferably in an amount of from about 50 to about 200 mg/m$^2$/day. In a certain embodiment, GM-CSF may be administered in an amount of from about 60 to about 500 mcg/m$^2$ intravenously over 2 hours, or from about 5 to about 12 mcg/m$^2$/day subcutaneously. In a specific embodiment, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In a certain embodiment, EPO may be administered subcutaneously in an amount of 10,000 Unit 3 times per week.

In another embodiment, a selective cytokine inhibitory drug is administered in an amount of from about 20 mg to about 1,200 mg/d alone or in combination with a second active agent to patients with metastatic melanoma (localized melanoma, including, but not limited to, ocular melanoma). In one embodiment, 3-(3,4-dimethoxy-phenyl)-3-(1-oxo-1,3-dihydro-isoindol-2-yl)-propionamide in an amount of from about 800 to about 1,200 mg/d and dacarbazine (DTIC) in an amount of from about 200 to about 1000 mg/m$^2$/d are administered to patients with metastatic melanoma (localized melanoma, including, but not limited to, ocular melanoma). In another embodiment, 3-(3,4-dimethoxy-phenyl)-3-(1-oxo-1,3-dihydro-isoindol-2-yl)-propionamide in an amount of about from 800 to 1,200 mg/d and temozolomide are administered to patients with metastatic melanoma (localized melanoma, including, but not limited to, ocular melanoma). In another embodiment, 3-(3,4-dimethoxy-phenyl)-3-(1-oxo-1,3-dihydro-isoindol-2-yl)-propionamide is administered in an amount of from about 200 to about 800 mg/d to patients with metastatic melanoma or localized melanoma whose disease has progressed on treatment with temozolomide, dacarbazine (DTIC), IL-2 and/or IFN. In a specific embodiment, 3-(3,4-dimethoxy-phenyl)-3-(1-oxo-1,3-dihydro-isoindol-2-yl)-propionamide is administered to patients with relapsed or refractory multiple myeloma in an amount of about 400 mg/d twice a day or about 800 mg/d four times a day in a combination with dexamethasone.

In another embodiment, a selective cytokine inhibitory drug is administered with melphalan and dexamethasone to patients with amyloidosis. In a specific embodiment, a selective cytokine inhibitory drug of the invention and steroids can be administered to patients with amyloidosis.

In another embodiment, a selective cytokine inhibitory drug is administered with gemcitabine and cisplatinum to patients with locally advanced or metastatic transitional cell bladder cancer.

In another embodiment, a selective cytokine inhibitory drug is administered in combination with a second active ingredient as follows: temozolomide to pediatric patients with relapsed or progressive brain tumors or recurrent neuroblastoma; celecoxib, etoposide and cyclophosphamide for relapsed or progressive CNS cancer; temodar to patients with recurrent or progressive meningioma, malignant meningioma, hemangiopericytoma, multiple brain metastases, relapased brain tumors, or newly diagnosed glioblastoma multiforms; irinotecan to patients with recurrent glioblastoma; carboplatin to pediatric patients with brain stem glioma; procarbazine to pediatric patients with progressive malignant gliomas; cyclophosphamide to patients with poor prognosis malignant brain tumors, newly diagnosed or recurrent glioblastoma multiforms; Gliadel® for high grade recurrent malignant gliomas; temozolomide and tamoxifen for anaplastic astrocytoma; or topotecan for gliomas, glioblastoma, anaplastic astrocytoma or anaplastic oligodendroglioma.

In another embodiment, a selective cytokine inhibitory drug is administered with methotrexate and cyclophosphamide to patients with metastatic breast cancer.

In another embodiment, a selective cytokine inhibitory drug is administered with temozolomide to patients with neuroendocrine tumors.

In another embodiment, a selective cytokine inhibitory drug is administered with gemcitabine to patients with recurrent or metastatic head or neck cancer. In another embodiment, a selective cytokine inhibitory drug is administered with gemcitabine to patients with pancreatic cancer.

In another embodiment, a selective cytokine inhibitory drug is administered to patients with colon cancer in combination with Arisa®, taxol and/or taxotere.

In another embodiment, a selective cytokine inhibitory drug is administered with capecitabine to patients with refractory colorectal cancer or patients who fail first line therapy or have poor performance in colon or rectal adenocarcinoma.

In another embodiment, a selective cytokine inhibitory drug is administered in combination with fluorouracil, leucovorin, and irinotecan to patients with Dukes C & D colorectal cancer or to patients who have been previously treated for metastatic colorectal cancer.

In another embodiment, a selective cytokine inhibitory drug is administered to patients with refractory colorectal cancer in combination with capecitabine, xeloda, and/or CPT-11.

In another embodiment, a selective cytokine inhibitory drug of the invention is administered with capecitabine and irinotecan to patients with refractory colorectal cancer or to patients with unresectable or metastatic colorectal carcinoma.

In another embodiment, a selective cytokine inhibitory drug is administered alone or in combination with interferon alpha or capecitabine to patients with unresectable or metastatic hepatocellular carcinoma; or with cisplatin and thiotepa to patients with primary or metastatic liver cancer.

In another embodiment, a selective cytokine inhibitory drug is administered in combination with pegylated interferon alpha to patients with Kaposi's sarcoma.

In another embodiment, a selective cytokine inhibitory drug is administered in combination with fludarabine, carboplatin, and/or topotecan to patients with refractory or relapsed or high-risk acuted myelogenous leukemia.

In another embodiment, a selective cytokine inhibitory drug is administered in combination with liposomal daunorubicin, topotecan and/or cytarabine to patients with unfavorable karotype acute myeloblastic leukemia.

In another embodiment, a selective cytokine inhibitory drug is administered in combination with gemcitabine and irinotecan to patients with non-small cell lung cancer. In one embodiment, a selective cytokine inhibitory drug is administered in combination with carboplatin and irinotecan to patients with non-small cell lung cancer. In one embodiment, a selective cytokine inhibitory drug is administered with doxetaxol to patients with non-small cell lung cancer who have been previously treated with carbo/VP 16 and radiotherapy.

In another embodiment, a selective cytokine inhibitory drug is administered in combination with carboplatin and/or taxotere, or in combination with carboplatin, paclitaxel and/or thoracic radiotherapy to patients with non-small cell lung cancer. In a specific embodiment, a selective cytokine inhibitory drug is administered in combination with taxotere to patients with stage IIIB or IV non-small cell lung cancer.

In another embodiment, a selective cytokine inhibitory drug of the invention is administered in combination with oblimersen (Genasense®) to patients with small cell lung cancer.

In another embodiment, a selective cytokine inhibitory drug is administered alone or in combination with a second active ingredient such as vinblastine or fludarabine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In another embodiment, a selective cytokine inhibitory drug is administered in combination with taxotere, IL-2, IFN, GM-CSF, and/or dacarbazine to patients with various types or stages of melanoma including, but not limited to, localized melanoma or metastatic melanoma such as ocular melanoma.

In another embodiment, a selective cytokine inhibitory drug is administered alone or in combination with vinorelbine to patients with malignant mesothelioma, or stage IIIB non-small cell lung cancer with pleural implants or malignant pleural effusion mesothelioma syndrome.

In another embodiment, a selective cytokine inhibitory drug is administered to patients with various types or stages of multiple myeloma in combination with dexamethasone, zoledronic acid, palmitronate, GM-CSF, biaxin, vinblastine, melphalan, busulphan, cyclophosphamide, IFN, palmidronate, prednisone, bisphosphonate, celecoxib, arsenic trioxide, PEG INTRON-A, vincristine, doxil, decadron, or a combination thereof.

In another embodiment, a selective cytokine inhibitory drug is administered to patients with relapsed or refractory multiple myeloma in combination with doxorubicin (Doxil®), vincristine and/or dexamethasone (Decadron®).

In another embodiment, a selective cytokine inhibitory drug is administered to patients with various types or stages of ovarian cancer such as peritoneal carcinoma, papillary serous carcinoma, refractory ovarian cancer or recurrent ovarian cancer, in combination with taxol, carboplatin, doxorubicin, gemcitabine, cisplatin, xeloda, paclitaxel, dexamethasone, or a combination thereof.

In another embodiment, a selective cytokine inhibitory drug is administered to patients with various types or stages of prostate cancer, in combination with xeloda, 5 FU/LV, gemcitabine, irinotecan plus gemcitabine, cyclophosphamide, vincristine, dexamethasone, GM-CSF, celecoxib, taxotere, ganciclovir, paclitaxel, adriamycin, docetaxel, estramustine, Emcyt, or a combination thereof.

In another embodiment, a selective cytokine inhibitory drug is administered to patients with various types or stages of renal cell cancer, in combination with capecitabine, IFN, tamoxifen, IL-2, GM-CSF, Celebrex®, or a combination thereof.

In another embodiment, a selective cytokine inhibitory drug is administered to patients with various types or stages of gynecologic, uterus or soft tissue sarcoma cancer in combination with IFN, a COX-2 inhibitor such as Celebrex®, and/or sulindac.

In another embodiment, a selective cytokine inhibitory drug is administered to patients with various types or stages of solid tumors in combination with celebrex, etoposide, cyclophosphamide, docetaxel, apecitabine, IFN, tamoxifen, IL-2, GM-CSF, or a combination thereof.

In another embodiment, a selective cytokine inhibitory drug is administered to patients with scelroderma or cutaneous vasculitis in combination with celebrex, etoposide, cyclophosphamide, docetaxel, apecitabine, IFN, tamoxifen, IL-2, GM-CSF, or a combination thereof.

This invention also encompasses a method of increasing the dosage of an anti-cancer drug or agent that can be safely and effectively administered to a patient, which comprises administering to a patient (e.g., a human) a selective cytokine inhibitory drug of the invention, or a pharmaceutically acceptable derivative, salt, solvate, clathrate, hydrate, or prodrug thereof. Patients that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of a selective cytokine inhibitory drug of the invention alleviates or reduces adverse effects which are of such severity that it would otherwise limit the amount of anticancer drug.

In one embodiment, a selective cytokine inhibitory drug of the invention can be administered orally and daily in an amount of from about 1 to about 5,000 mg, from about 10 to about 2,500 mg, from about 25 to about 2,500 mg, from about 100 to about 1,200 mg, or from about 100 to about 800 mg prior to, during, or after the occurrence of the adverse effect associated with the administration of an anti-cancer drug to a patient. In a particular embodiment, a selective cytokine inhibitory drug of the invention is administered in combination with specific agents such as heparin, aspirin, coumadin, or G-CSF to avoid adverse effects that are associated with anti-cancer drugs such as but not limited to neutropenia or thrombocytopenia.

In one embodiment, a selective cytokine inhibitory drug of the invention can be administered to patients with diseases and disorders associated with, or characterized by, undesired angiogenesis in combination with additional active ingredients including but not limited to anti-cancer drugs, anti-inflammatories, antihistamines, antibiotics, and steroids.

In another embodiment, this invention encompasses a method of treating, preventing and/or managing cancer, which comprises administering a selective cytokine inhibitory drug of the invention, or a pharmaceutically acceptable salt, solvate, hydrate, stereoisomer, clathrate, or prodrug thereof, in conjunction with (e.g. before, during, or after) conventional therapy including, but not limited to, surgery, immunotherapy, biological therapy, radiation therapy, or other non-drug based therapy presently used to treat, prevent or manage cancer. The combined use of the selective cytokine inhibitory drugs of the invention and conventional therapy may provide a unique treatment regimen that is unexpectedly effective in certain patients. Without being limited by theory, it is believed that selective cytokine inhibitory drugs of the invention may provide additive or synergistic effects when given concurrently with conventional therapy.

In another embodiment, this invention encompasses a method of treating, preventing and/or managing diseases and disorders associated with, or characterized by, undesired angiogenesis, which comprises administering a selective cytokine inhibitory drug, or a pharmaceutically acceptable salt, solvate, hydrate, stereoisomer, clathrate, or prodrug thereof, in conjunction with (e.g. before, during, or after) conventional therapy including, but not limited to, surgery, immunotherapy, biological therapy, radiation therapy, or other non-drug based therapy presently used to treat, prevent or manage diseases and disorders associated with, or characterized by, undesired angiogenesis. The combined use of the selective cytokine inhibitory drug and conventional therapy may provide a unique treatment regimen that is unexpectedly effective in certain patients. Without being limited by theory, it is believed that the selective cytokine inhibitory drug may provide additive or synergistic effects when given concurrently with conventional therapy.

As discussed elsewhere herein, the invention encompasses a method of reducing, treating and/or preventing adverse or undesired effects associated with conventional therapy including, but not limited to, surgery, chemotherapy, radiation therapy, hormonal therapy, biological therapy and immunotherapy. One or more selective cytokine inhibitory drugs of the invention and other active ingredient can be administered to a patient prior to, during, or after the occurrence of the adverse effect associated with conventional therapy.

In one embodiment, a selective cytokine inhibitory drug of the invention can be administered in an amount of from about 1 to about 5,000 mg, from about 10 to about 2,500 mg, from about 25 to about 2,500 mg, from about 100 to about 1,200 mg, or from about 100 to about 800 mg orally and daily alone, or in combination with a second active agent disclosed herein (see, e.g., section 4.2), prior to, during, or after the use of conventional therapy.

In a specific embodiment of this method, a selective cytokine inhibitory drug of the invention and doxetaxol are administered to patients with non-small cell lung cancer who were previously treated with carbo/VP 16 and radiotherapy.

4.3.2. Use with Transplantation Therapy

Compounds of the invention can be used to reduce the risk of Graft Versus Host Disease (GVHD). Therefore, the invention encompasses a method of treating, preventing and/or managing cancer, which comprises administering the selective cytokine inhibitory drug of the invention, or a pharmaceutically acceptable salt, solvate, hydrate, stereoisomer, clathrate, or prodrug thereof, in conjunction with transplantation therapy.

As those of ordinary skill in the art are aware, the treatment of cancer is often based on the stages and mechanism of the disease. For example, as inevitable leukemic transformation develops in certain stages of cancer, transplantation of peripheral blood stem cells, hematopoietic stem cell preparation or bone marrow may be necessary. The combined use of the selective cytokine inhibitory drug of the invention and transplantation therapy provides a unique and unexpected synergism. In particular, a selective cytokine inhibitory drug of the invention exhibits activity that may provide additive or synergistic effects when given concurrently with transplantation therapy in patients with cancer.

A selective cytokine inhibitory drug of the invention can work in combination with transplantation therapy reducing complications associated with the invasive procedure of transplantation and risk of GVHD. This invention encompasses a method of treating, preventing and/or managing cancer which comprises administering to a patient (e.g., a human) a selective cytokine inhibitory drug of the invention, or a pharmaceutically acceptable salt, solvate, hydrate, stereoisomer, clathrate, or prodrug thereof, before, during, or after the transplantation of umbilical cord blood, placental blood, peripheral blood stem cell, hematopoietic stem cell preparation or bone marrow. Examples of stem cells suitable for use in the methods of the invention are disclosed in U.S. patent application Ser. No. 10/411,655, filed Apr. 11, 2003 by R. Hariri et al., the entirety of which is incorporated herein by reference.

In another embodiment, this invention encompasses a method of treating, preventing and/or managing diseases and disorders associated with, or characterized by, undesired angiogenesis, which comprises administering to a patient (e.g., a human) a selective cytokine inhibitory drug, or a pharmaceutically acceptable salt, solvate, hydrate, stereoisomer, clathrate, or prodrug thereof, before, during, or after the transplantation of umbilical cord blood, placental blood, peripheral blood stem cell, hematopoietic stem cell preparation or bone marrow.

In one embodiment of this method, a selective cytoline inhibitory drug of the invention is administered to patients with multiple myeloma before, during, or after the transplantation of autologous peripheral blood progenitor cell.

In another embodiment, a selective cytokine inhibitory drug is administered to patients with relapsing multiple myeloma after the stem cell transplantation.

In another embodiment, a selective cytokine inhibitory drug and prednisone are administered as maintenance therapy to patients with multiple myeloma following the transplantation of autologous stem cell.

In another embodiment, a selective cytokine inhibitory drug and dexamethasone are administered as salvage therapy for low risk post transplantation to patients with multiple myeloma.

In another embodiment, a selective cytokine inhibitory drug and dexamethasone are administered as maintenance therapy to patients with multiple myeloma following the transplantation of autologous bone marrow.

In another embodiment, a selective cytokine inhibitory drug is administered following the administration of high dose of melphalan and the transplantation of autologous stem cell to patients with chemotherapy responsive multiple myeloma.

In another embodiment, a selective cytokine inhibitory drug and PEG INTRO-A are administered as maintenance therapy to patients with multiple myeloma following the transplantation of autologous CD34-selected peripheral stem cell.

In another embodiment, a selective cytokine inhibitory drug is administered with post transplant consolidation chemotherapy to patients with newly diagnosed multiple myeloma to evaluate anti-angiogenesis.

In another embodiment, a selective cytokine inhibitory drug and dexamethasone are administered as maintenance therapy after DCEP consolidation, following the treatment with high dose of melphalan and the transplantation of peripheral blood stem cell to 65 years of age or older patients with multiple myeloma.

4.3.3. Cycling Therapy

In certain embodiments, the prophylactic or therapeutic agents of the invention are cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one or more of the therapies, and/or improves the efficacy of the treatment.

Consequently, in one specific embodiment of the invention, a selective cytokine inhibitory drug of the invention is administered daily in a single or divided doses in a four to six week cycle with a rest period of about a week or two weeks. The invention further allows the frequency, number, and length of dosing cycles to be increased. Thus, another specific embodiment of the invention encompasses the administration of a selective cytokine inhibitory drug of the invention for more cycles than are typical when it is administered alone. In yet another specific embodiment of the invention, a selective cytokine inhibitory drug of the invention is administered for a greater number of cycles that would typically cause dose-limiting toxicity in a patient to whom a second active ingredient is not also being administered.

In one embodiment, a selective cytokine inhibitory drug of the invention is administered daily and continuously for three or four weeks at a dose of from about 1 to about 5,000 mg/d followed by a break of one or two weeks. 3-(3,4-Dimethoxy-phenyl)-3-(1-oxo-1,3-dihydro-isoindol-2-yl)-propionamide is preferably administered daily and continuously at an initial dose of 1 to 5 mg/d with dose escalation (every week) by 10 to 100 mg/d to a maximum dose of 5,000 mg/d for as long as therapy is tolerated. In a particular embodiment, the compound is administered in an amount of about 400, 800, or 1,200 mg/day, preferably in an amount of about 800 mg/day for three to four weeks, followed by one week or two weeks of rest in a four or six week cycle.

In one embodiment of the invention, a selective cytokine inhibitory drug of the invention and a second active ingredient are administered orally, with administration of a selective cytokine inhibitory drug of the invention occurring 30 to 60 minutes prior to a second active ingredient, during a cycle of four to six weeks. In another embodiment of the invention, the combination of a selective cytokine inhibitory drug of the invention and a second active ingredient is administered by intravenous infusion over about 90 minutes every cycle. In a specific embodiment, one cycle comprises the administration of from about 400 to about 800 mg/day of 3-(3,4-dimethoxy-phenyl)-3-(1-oxo-1,3-dihydro-isoindol-2-yl)-propionamide and from about 50 to about 200 mg/m$^2$/day of a second active ingredient daily for 3 to 4 weeks and then one or two weeks of rest. In another specific embodiment, each cycle comprises the administration of from about 200 to about 400 mg/day of 3-(3,4-dimethoxy-phenyl)-3-(1-oxo-1,3-dihydro-isoindol-2-yl)-propionamide and from about 50 to about 200 mg/m$^2$/day of a second active ingredient for three to four weeks followed by one or two weeks of rest. Typically, the number of cycles during which the combinatorial treatment is administered to a patient will be from about one to about 24 cycles, more typically from about two to about 16 cycles, and even more typically from about four to about eight cycles.

4.4. Pharmaceutical Compositions

Pharmaceutical compositions can be used in the preparation of individual, single unit dosage forms. Pharmaceutical compositions and dosage forms of the invention comprise a selective cytokine inhibitory drug of the invention, or a pharmaceutically acceptable salt, solvate, hydrate, stereoisomer, clathrate, or prodrug thereof. Pharmaceutical compositions and dosage forms of the invention can further comprise one or more excipients.

Pharmaceutical compositions and dosage forms of the invention can also comprise one or more additional active ingredients. Consequently, pharmaceutical compositions and dosage forms of the invention comprise the active ingredients disclosed herein (e.g., a selective cytokine inhibitory drug and a second active agent). Examples of optional second, or additional, active ingredients are disclosed herein (see, e.g., section 4.2).

Single unit dosage forms of the invention are suitable for oral, mucosal (e.g. nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the *U.S. Pharmacopeia* (USP) 25-NF20 2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise a selective cytokine inhibitory drug of the invention or a pharmaceutically acceptable salt, solvate, hydrate, stereoisomer, clathrate, or prodrug hereof in an amount of from about 0.10 to about 150 mg. Typical dosage forms comprise a selective cytokine inhibitory drug of the invention or a pharmaceutically acceptable salt, solvate, hydrate, stereoisomer, clathrate, or prodrug thereof in an amount of about 0.1, 1, 2, 5, 7.5, 10, 12.5, 15, 17.5, 20, 25, 50, 100, 150 or 200 mg. In a particular embodiment, a preferred dosage form comprises 4-(amino)-2-(2,6-dioxo(3-piperidyl))-isoindoline-1,3-dione (Actimid™) in an amount of about 1, 2, 5, 10, 25 or 50 mg. In a specific embodiment, a preferred dosage form comprises 3-(3,4-dimethoxy-phenyl)-3-(1-oxo-1,3-dihydro-isoindol-2-yl)-propionamide in an amount of about 5, 10, 25 or 50 mg. Typical dosage forms comprise the second active ingredient in an amount of 1 to about 1000 mg, from about 5 to about 500 mg, from about 10 to about 350 mg, or from about 50 to about 200 mg. Of course, the specific amount of the anti-cancer drug will depend on the specific agent used, the type of cancer being treated or managed, and the amount(s) of a selective cytokine inhibitory drug of the invention and any optional additional active agents concurrently administered to the patient.

4.4.1. Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, PA), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises a selective cytokine inhibitory drug of the invention, anhydrous lactose, microcrystalline cellulose, polyvinylpyrrolidone, stearic acid, colloidal anhydrous silica, and gelatin.

4.4.2. Delayed Release Dosage Forms

Active ingredients of the invention can be administered by controlled release means or by delivery devices that are well known to those of ordinary skill in the art. Examples include, but are not limited to, those described in U.S. Pat.

Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.4.3. Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention. For example, cyclodextrin and its derivatives can be used to increase the solubility of a selective cytokine inhibitory drug of the invention and its derivatives. See, e.g., U.S. Pat. No. 5,134,127, which is incorporated herein by reference.

4.4.4. Topical and Mucosal Dosage Forms

Topical and mucosal dosage forms of the invention include, but are not limited to, sprays, aerosols, solutions, emulsions, suspensions, eye drops or other ophthalmic preparations, or other forms known to one of skill in the art. See, e.g., *Remington's Pharmaceutical Sciences*, $16^{th}$ and $18^{th}$ eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, $16^{th}$ and $18^{th}$ eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further the adjust the properties of the resulting composition.

4.4.5. Kits

Typically, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a dosage form of a selective cytokine inhibitory drug of the invention, or a pharmaceutically acceptable salt, solvate, hydrate, stereoisomer, prodrug, or clathrate thereof. Kits encompassed by this invention can further comprise additional active ingredients such as oblimersen (Genasense®), melphalan, G-CSF, GM-CSF, EPO, topotecan, dacarbazine, irinotecan, taxotere, IFN, COX-2 inhibitor, pentoxifylline, ciprofloxacin, dexamethasone, IL2, IL8, IL18, Ara-C, vinorelbine, isotretinoin, 13 cis-retinoic acid, or a pharmacologically active mutant or derivative thereof, or a combination thereof. Examples of the additional active ingredients include, but are not limited to, those disclosed herein (see, e.g., section 5.2).

Kits of the invention can further comprise devices that are used to administer the active ingredients. Examples of such devices include, but are not limited to, syringes, drip bags, patches, and inhalers.

Kits of the invention can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

Certain embodiments of the invention are illustrated by the following non-limiting examples.

5.1. Modulation of Cytokine Production

A series of non-clinical pharmacology and toxicology studies have been performed to support the clinical evaluation of a selective cytokine inhibitory drug of the invention in human subjects. These studies were performed in accordance with internationally recognized guidelines for study design and in compliance with the requirements of Good Laboratory Practice (GLP), unless otherwise noted.

In a specific embodiment, the pharmacological properties of 3-(3,4-dimethoxy-phenyl)-3-(1-oxo-1,3-dihydro-isoindol-2-yl)-propionamide are characterized in in vitro studies. Studies examine the effects of the compound on the production of various cytokines. Inhibition of TNF-α production following LPS-stimulation of human PBMC and human whole blood by the compound is investigated in vitro. In vitro studies suggest a pharmacological activity profile for 3-(3,4-dimethoxy-phenyl)-3-(1-oxo-1,3-dihydro-isoindol-2-yl)-propionamide is five to fifty times more potent than thalidomide. The pharmacological effects of 3-(3,4-dimethoxy-phenyl)-3-(1-oxo-1,3-dihydro-isoindol-2-yl)-propionamide may derive from its action as an inhibitor of the generation of inflammatory cytokines.

5.2. Inhibition of MM Cell Proliferation

The ability of a selective cytokine inhibitory drug to effect the proliferation of multiple myeloma (MM) cell lines is investigated in an in vitro study. Uptake [$^3$H]-thymidine by different MM cell lines (MM.1S, Hs Sultan, U266 and RPMI-8226) is measured as an indicator of cell proliferation. Cells are incubated in the presence of compound for 48 hours; [$^3$H]-thymidine is included for the last 8 hours of the incubation period. In a specific embodiment, 3-(3,4-dimethoxy-phenyl)-3-(1-oxo-1,3-dihydro-isoindol-2-yl)-propionamide is added to MM.1S and Hs Sultan cells. The uptake [$^3$H]-thymidine by different MM cell lines is measured.

5.3. In Vivo LPS-Induced TNF-α Production Assay

Male CD rats procured from Charles River Laboratories at seven weeks of age are allowed to acclimate for one week prior to use. A lateral tail vein is cannulated percutaneously with a 22-gage over-the-needle catheter under brief isoflurane anesthesia. Rats are administered a selective cytokine inhibitory drug of the invention either by intravenous injection via the tail vein catheter or oral gavage 15 to 180 min prior to injection of 0.05 mg/kg LPS (*E. Coli* 055:B5). Catheters are flushed with 2.5 mL/kg of normal injectable saline. Blood is collected via cardiac puncture 90 minutes after LPS challenge. Plasma is prepared using lithium heparin separation tubes and frozen at −80° C. until analyzed. TNF-α levels are determined using a rat specific TNF-α ELISA kit (Busywork). The $ED_{50}$ values are calculated as the dose of the selective cytokine inhibitory drug of the invention at which the TNF-α production is reduced to 50% of the control value.

5.4. Toxicology Studies

The effects of 3-(3,4-dimethoxy-phenyl)-3-(1-oxo-1,3-dihydro-isoindol-2-yl)-propionamide on cardiovascular and respiratory function are investigated in anesthetized dogs. Two groups of Beagle dogs (2/sex/group) are used. One group receives three doses of vehicle only and the other receives three ascending doses of the compound (200, 400, and 800 mg/kg). In all cases, doses of the compound or vehicle are successively administered via infusion through the jugular vein separated by intervals of at least 30 minutes.

The cardiovascular and respiratory changes induced by 3-(3,4-dimethoxy-phenyl)-3-(1-oxo-1,3-dihydro-isoindol-2-yl)-propionamide are minimal at all doses when compared to the vehicle control group. The only statistically significant difference between the vehicle and treatment groups is a small increase in arterial blood pressure following administration of the low dose of 3-(3,4-dimethoxy-phenyl)-3-(1-oxo-1,3-dihydro-isoindol-2-yl)-propionamide. This effect lasts approximately 15 minutes and is not seen at higher doses. Deviations in femoral blood flow, respiratory parameters, and Qtc interval are common to both the control and treated groups and are not considered treatment-related.

5.5. Cycling Therapy in Patients

In a specific embodiment, a selective cytokine inhibitory drug of the invention are cyclically administered to patients with cancer. Cycling therapy involves the administration of a first agent for a period of time, followed by a rest for a period of time and repeating this sequential administration. Cycling therapy can reduce the development of resistance to one or more of the therapies, avoid or reduce the side effects of one of the therapies, and/or improves the efficacy of the treatment.

In a specific embodiment, prophylactic or therapeutic agents are administered in a cycle of about four to six weeks, about once or twice every day. One cycle can comprise the administration of a therapeutic on prophylactic agent for three to four weeks and at least one week or two weeks of rest. The number of cycles administered is from about one to about 24 cycles, more typically from about two to about 16 cycles, and more typically from about four to about eight cycles.

For example, in a cycle of four weeks, on day 1, the administration of 800 mg/d of 3-(3,4-dimethoxy-phenyl)-3-(1-oxo-1,3-dihydro-isoindol-2-yl)-propionamide is started. On day 22, the administration of the compound is stopped for a week of rest. On day 29, the administration of 800 mg/d of the compound is begun.

5.6. Clinical Studies in Patients with Relapsed Multiple Myeloma

Patients with relapsed and refractory Dune-Salmon stage III multiple myeloma, who have either failed at least three previous regimens or presented with poor performance status, neutropenia or thrombocytopenia, are treated with up to four cycles of combination melphalan (50 mg intravenously), a selective cytokine inhibitory drug of the invention (about 1 to 5,000 mg orally daily), and dexamethasone (40 mg/day orally on days 1 to 4) every four to six weeks. Maintenance treatment consisting of daily a selective cytokine inhibitory drug of the invention and monthly dexamethasone are continued until the disease progression. The therapy comprising the administration of a selective cytokine inhibitory drug of the invention in combination with melphalan and dexamethasone is highly active and generally tolerated in heavily pretreated multiple myeloma patients whose prognosis is otherwise poor.

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of treating chronic uveitis, which comprises administering to a patient in need of such treatment a therapeutically effective amount of cyclopropyl-N-{2-[(1S)-1-(3-ethoxy-4-methoxyphenyl)-2-(methylsulfonyl)ethyl]-3-oxoisoindoline-4-yl}carboxamide, which has the following structure:

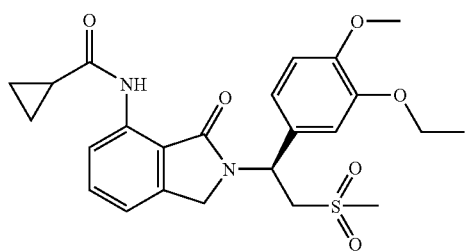

or a pharmaceutically acceptable salt, or solvate thereof.

2. A method of treating chronic uveitis, which comprises administering to a patient in need of such treatment a therapeutically effective amount of cyclopropyl-N-{2-[(1S)-1-(3-ethoxy-4-methoxyphenyl)-2-(methylsulfonyl)ethyl]-3-oxoisoindoline-4-yl}carboxamide, which has the following structure:

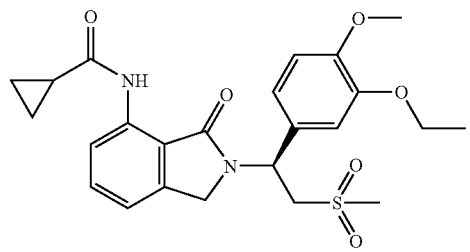

or a pharmaceutically acceptable salt, or solvate thereof, and a therapeutically effective amount of a second active ingredient.

3. The method of claim 2, wherein the second active ingredient is cytokine, anti-cancer agent, cox-2 inhibitor, or a combination thereof.

4. The method of claim 2, wherein the second active ingredient is oblimersen, melphalan, G-CSF, GM-CSF, EPO, topotecan, pentoxifylline, taxotere, irinotecan, a COX-2 inhibitor, ciprofloxacin, dexamethasone, doxorubicin, vincristine, IL 2, IFN, dacarbazine, Ara-C, vinorelbine, isotretinoin, or a pharmaceutically acceptable salt, solvate, or stereoisomer thereof, or a combination thereof.

5. The method of claim 1 or 2, wherein the compound is enantiomerically pure.

6. The method according to claim 1 or 2, wherein the compound is administered in an amount of from about 1 to about 10,000 mg per day.

7. The method of claim 6, wherein the compound is administered in an amount of about 10, 25, 50, 100, 200 or 300 mg per day.

8. The method of claim 6, wherein the compound is orally administered.

9. The method of claim 6, wherein the compound is administered in a capsule.

10. The method of claim 9, wherein the compound is administered in 50 mg or 100 mg of a capsule.

11. The method of claim 6, wherein the compound is topically administered.

12. The method of claim 11, wherein the compound is administered in a spray, aerosol, solution, suspension or eye drop.

13. The method of claim 3, wherein the second active ingredient is prednisone.

* * * * *